United States Patent
Hashimoto et al.

(10) Patent No.: US 10,401,748 B2
(45) Date of Patent: Sep. 3, 2019

(54) TONER

(71) Applicant: CANON KABUSHIKI KAISHA, Tokyo (JP)

(72) Inventors: Takeshi Hashimoto, Moriya (JP); Nozomu Komatsu, Toride (JP); Yuto Onozaki, Saitama (JP); Akifumi Matsubara, Narashino (JP); Ichiro Kanno, Kashiwa (JP); Hitoshi Sano, Tokyo (JP); Tsubasa Fujisaki, Toride (JP); Masayuki Hama, Toride (JP); Takakuni Kobori, Toride (JP); Hiroyuki Fujikawa, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/600,929

(22) Filed: May 22, 2017

(65) Prior Publication Data
US 2017/0343911 A1 Nov. 30, 2017

(30) Foreign Application Priority Data
May 26, 2016 (JP) ................. 2016-105086

(51) Int. Cl.
G03G 9/087 (2006.01)
C08G 63/12 (2006.01)
C08G 63/85 (2006.01)
G01N 15/08 (2006.01)
G03G 9/08 (2006.01)
G03G 9/097 (2006.01)

(52) U.S. Cl.
CPC ......... *G03G 9/08795* (2013.01); *C08G 63/12* (2013.01); *C08G 63/85* (2013.01); *G01N 15/0826* (2013.01); *G03G 9/081* (2013.01); *G03G 9/08755* (2013.01); *G03G 9/08793* (2013.01); *G03G 9/08797* (2013.01); *G03G 9/09708* (2013.01); *G03G 9/09783* (2013.01)

(58) Field of Classification Search
CPC ................................ G03G 9/08755
See application file for complete search history.

(56) References Cited

U.S. PATENT DOCUMENTS

| | | | |
|---|---|---|---|
| 5,424,810 A | 6/1995 | Tomiyama et al. |
| 5,464,722 A | 11/1995 | Tomiyama et al. |
| 5,700,616 A | 12/1997 | Kasuya et al. |
| 5,712,073 A | 1/1998 | Katada et al. |
| 5,968,701 A | 10/1999 | Onuma et al. |
| 5,972,553 A | 10/1999 | Katada et al. |
| 6,002,895 A | 12/1999 | Kasuya et al. |
| 6,007,957 A | 12/1999 | Kobori et al. |
| 6,020,102 A | 2/2000 | Fujimoto et al. |
| 6,120,961 A | 9/2000 | Tanikawa et al. |
| 6,156,471 A | 12/2000 | Kobori et al. |
| 6,203,959 B1 | 3/2001 | Tanikawa et al. |
| 6,235,441 B1 | 5/2001 | Tanikawa et al. |
| 6,430,384 B2 | 8/2002 | Hama et al. |
| 6,653,036 B1 | 11/2003 | Tanikawa et al. |
| 6,670,087 B2 | 12/2003 | Fujikawa et al. |
| 6,751,424 B2 | 6/2004 | Komatsu et al. |
| 6,808,852 B2 | 10/2004 | Hotta et al. |
| 7,112,395 B2 | 9/2006 | Ida et al. |
| 7,135,263 B2 | 11/2006 | Kawakami et al. |
| 7,147,980 B2 | 12/2006 | Itakura et al. |
| 7,147,981 B2 | 12/2006 | Fujikawa et al. |
| 7,279,262 B2 | 10/2007 | Fujikawa et al. |
| 7,288,348 B2 | 10/2007 | Hayami et al. |
| 7,297,455 B2 | 11/2007 | Fujikawa et al. |
| 7,300,733 B2 | 11/2007 | Sugahara et al. |
| 7,361,441 B2 | 4/2008 | Itakura et al. |
| 7,396,626 B2 | 7/2008 | Fujikawa et al. |
| 7,396,629 B2 | 7/2008 | Baba et al. |
| 7,442,478 B2 | 10/2008 | Itakura et al. |
| 7,452,647 B2 | 11/2008 | Hayami et al. |
| 7,611,813 B2 | 11/2009 | Ida et al. |
| 7,855,042 B2 | 12/2010 | Kobori et al. |
| 7,858,283 B2 | 12/2010 | Ishigami et al. |
| 7,927,775 B2 | 4/2011 | Komatsu et al. |
| 7,939,233 B2 | 5/2011 | Inoue et al. |
| 8,017,292 B2 | 9/2011 | Sabu et al. |
| 8,137,886 B2 | 3/2012 | Baba et al. |
| 8,142,972 B2 | 3/2012 | Hotta et al. |
| 8,288,069 B2 | 10/2012 | Fujikawa et al. |
| 8,921,023 B2 | 12/2014 | Baba et al. |

(Continued)

FOREIGN PATENT DOCUMENTS

| | | |
|---|---|---|
| JP | 2008-281882 | 11/2008 |
| JP | 2009-217053 | 9/2009 |

OTHER PUBLICATIONS

U.S. Appl. No. 15/495,196, Nozomu Komatsu, filed Apr. 24, 2017.
U.S. Appl. No. 15/498,966, Yuto Onozaki, filed Apr. 27, 2017.
U.S. Appl. No. 15/611,865, Ichiro Kanno, filed Jun. 2, 2017.

*Primary Examiner* — Peter L Vajda
(74) *Attorney, Agent, or Firm* — Venable LLP

(57) ABSTRACT

A toner comprises a toner particle containing an amorphous polyester, wherein the amorphous polyester contains an amorphous polyester 1, the amorphous polyester contains a tin compound and a titanium compound, a Sn/Ti abundance ratio between Sn and Ti in the amorphous polyester according to x-ray fluorescence analysis is 20/80 to 80/20, and a weight-average molecular weight Mw1 of the amorphous polyester 1 according to measurement by gel permeation chromatography (GPC) is Mw1<7,000.

4 Claims, No Drawings

(56) References Cited

U.S. PATENT DOCUMENTS

| | | |
|---|---|---|
| 8,927,188 B2 | 1/2015 | Naka et al. |
| 8,986,914 B2 | 3/2015 | Fujikawa et al. |
| 9,034,549 B2 | 5/2015 | Shiotari et al. |
| 9,058,924 B2 | 6/2015 | Komatsu et al. |
| 9,063,443 B2 | 6/2015 | Ishigami et al. |
| 9,152,088 B1 | 10/2015 | Kobori et al. |
| 9,348,253 B2 | 5/2016 | Kanno et al. |
| 9,372,420 B2 | 6/2016 | Mizo et al. |
| 9,417,540 B2 | 8/2016 | Hashimoto et al. |
| 9,500,975 B2 | 11/2016 | Sugahara et al. |
| 9,594,323 B2 | 3/2017 | Fujikawa et al. |
| 9,599,920 B2 | 3/2017 | Sugahara et al. |
| 9,651,883 B2 | 5/2017 | Hama et al. |
| 9,665,021 B2 | 5/2017 | Ohtsu et al. |
| 9,665,023 B2 | 5/2017 | Kamae et al. |
| 9,665,026 B2 | 5/2017 | Iwasaki et al. |
| 9,671,707 B2 | 6/2017 | Minagawa et al. |
| 2004/0241565 A1* | 12/2004 | Kishiki .................. C08G 63/85 430/109.4 |
| 2008/0187854 A1* | 8/2008 | Yoshida ............... G03G 9/0804 430/109.4 |
| 2009/0011356 A1* | 1/2009 | Tomita .................. C08G 63/85 430/109.4 |
| 2009/0035679 A1* | 2/2009 | Ogawa .................. G03G 9/081 430/106.2 |
| 2009/0246675 A1 | 10/2009 | Nakamura et al. |
| 2010/0028796 A1 | 2/2010 | Nakamura et al. |
| 2010/0183971 A1 | 7/2010 | Fujikawa et al. |
| 2013/0244159 A1 | 9/2013 | Ishigami et al. |
| 2014/0134535 A1 | 5/2014 | Baba et al. |
| 2014/0137428 A1 | 5/2014 | Takenaka et al. |
| 2014/0329176 A1 | 11/2014 | Kanno et al. |
| 2016/0109820 A1 | 4/2016 | Hashimoto et al. |
| 2016/0306301 A1 | 10/2016 | Sugahara et al. |
| 2016/0363877 A1 | 12/2016 | Hama et al. |
| 2016/0363889 A1 | 12/2016 | Onozaki et al. |

\* cited by examiner

TONER

BACKGROUND OF THE INVENTION

Field of the Invention

The present invention relates to a toner used in electrophotographic systems, electrostatic recording systems, electrostatic printing systems, and toner jet systems.

Description of the Related Art

The extensive spread of full-color copiers that use electrophotographic systems has been accompanied by additional increases in the demand for higher printing speeds and greater energy savings. Art for bringing about a more rapid melting of the toner in the fixing step has been investigated in order to accommodate high-speed printing. In addition, in order to accommodate greater energy savings, art for causing the toner to undergo fixing at lower fixation temperatures has been investigated in order to lower the power consumption in the fixing step.

Methods for accommodating high-speed printing and improving the low-temperature fixability of a toner include lowering the glass transition temperature and/or softening point of the binder resin in the toner and using a binder resin that exhibits a sharp melt property. In order to provide a sharp melt property, investigations have been carried out into the use of polyester resin for the binder resin and into reducing the molecular weight of the polyester resin. However, the hot offset resistance and/or the fixing wraparound resistance has ended up being reduced. In order to solve this problem, investigations have been carried out into the toner that uses two species of binder resin, i.e., a high molecular weight resin and a low molecular weight resin.

For example, Japanese Patent Application Laid-open No. 2009-217053 discloses a toner for electrostatic charge development that contains at least two types of polyester resin, a colorant, and a release agent, and for which GSDp-under—a number-average particle size distribution index on the small particle side—is in a specific range and MwT and MwS satisfy a specific relationship where D50T is the volume-average particle diameter of the entire toner, MwT is the weight-average molecular weight of the toner, and MwS is the weight-average molecular weight of the toner provided by classification of the toner into the volume-average particle diameter range of at least ($\frac{1}{5}$)×D50T and not more than ($\frac{2}{3}$)×D50T.

In addition, Japanese Patent Application Laid-open No. 2008-281882 discloses a toner that is characteristically provided by the emulsification or dispersion and aggregation in an aqueous medium of particles comprising at least polyester resin particles wherein the polyester resin particles contain a polyester resin and the polyester resin is provided by the condensation of a carboxylic acid component containing refined rosin and an alcohol component that contains at least 65 mol % 1,2-propanediol in the divalent alcohol component, the softening point of the polyester resin is at least 80° C. and less than 120° C., and the toner contains a colorant and a release agent.

SUMMARY OF THE INVENTION

There has been a constantly increasing demand in recent years for greater energy savings from copiers and for a maximization of productivity through reducing, to the greatest extent possible, various adjustments in the copier. With regard to the toner, there is also demand for a toner that enables fixing at lower fixation temperatures, that is free of hot offset and wraparound even at high temperatures, and that has a broad fixable temperature range. A toner that can satisfy these capabilities has not been obtained under the indicated circumstances.

An object of the present invention is to provide a toner that solves the aforementioned problems. More specifically, an object of the present invention is to provide a toner that exhibits low-temperature fixability, an excellent hot offset resistance, and an excellent fixing wraparound resistance.

The toner of the present invention comprises a toner containing an amorphous polyester, wherein the amorphous polyester contains an amorphous polyester 1, the amorphous polyester contains a tin compound and a titanium compound, a Sn/Ti abundance ratio between the Sn and Ti in the amorphous polyester according to x-ray fluorescence analysis is 20/80 to 80/20, and a weight-average molecular weight Mw1 of the amorphous polyester 1 according to measurement by gel permeation chromatography (GPC) is Mw1<7,000.

The present invention can provide a toner that exhibits low-temperature fixability, an excellent hot offset resistance, and an excellent fixing wraparound resistance.

Further features of the present invention will become apparent from the following description of exemplary embodiments.

DESCRIPTION OF THE EMBODIMENTS

Unless specifically indicated otherwise, expressions such as "at least XX and not more than YY" and "XX to YY" that show numerical value ranges refer in the present invention to numerical value ranges that include the lower limit and upper limit that are the end points.

The toner of the present invention comprises a toner particle that contains an amorphous polyester, wherein the amorphous polyester contains an amorphous polyester 1, the amorphous polyester contains a tin compound and a titanium compound, the Sn/Ti abundance ratio between the Sn and Ti in the amorphous polyester according to x-ray fluorescence analysis is 20/80 to 80/20, and the weight-average molecular weight Mw1 of the amorphous polyester 1 according to measurement by gel permeation chromatography (GPC) is Mw1<7,000.

Investigations by the present inventors demonstrated that a low molecular weight component contained in the amorphous polyester was one factor of the reduction in the hot offset and the reduction in the fixing wraparound resistance. This low molecular weight component is a polyester component having a low degree of polymerization and a molecular weight of not more than approximately 2,000, and it tends to substantially increase when the weight-average molecular weight of the amorphous polyester is less than 7,000. The ill effects on the fixing performance can be relaxed when the weight-average molecular weight of the amorphous polyester is increased; however, the sharp melt property of the amorphous polyester resin then ends up being reduced. As a result of focused investigations, the present inventors discovered that, by controlling the abundance ratio between the element tin and the element titanium in the amorphous polyester resin into a certain range, the hot offset resistance and the fixing wraparound resistance were improved while the low-temperature fixability could be retained unchanged. The present invention was achieved based on this discovery. In the present invention, the amorphous polyester contains a tin compound and a titanium compound.

The mechanism through which the effects of the present invention are exhibited is hypothesized to be as follows. Tin compounds often have the ability to readily react with a plurality of carboxy groups. Titanium compounds, on the other hand, often have the ability to readily react with a plurality of hydroxy groups. Moreover, it is frequently the case that much of the low molecular weight component of the amorphous polyester has the carboxy group at one terminal and the hydroxy group at the other terminal. It is thought that, by having a tin compound and a titanium compound be copresent in a certain proportion in the amorphous polyester, reactions between the low molecular weight component of the amorphous polyester and the tin compound and titanium compound then occur during the toner production process.

In these reactions, the carboxy group at the one terminal of the low molecular weight component of the amorphous polyester reacts with the tin compound and the hydroxy group at the other terminal reacts with the titanium compound. It is thought that, since the tin compound and titanium compound each have a plurality of reaction sites, an increase in the molecular weight occurs through the successive crosslinking of the low molecular weight component of the amorphous polyester via the tin compound and titanium compound. This is thought to result in a substantial improvement in the hot offset resistance and fixing wraparound resistance.

These crosslinking reactions are thought to occur in the step in which heat is applied to the system, i.e., in the melt-kneading step when the toner production method is a pulverization method and in the aggregation step or fusion step for the dispersed particles when the toner production method is an aggregation method.

In addition, when only the tin compound or only the titanium compound is present in the amorphous polyester, the increase in molecular weight cannot occur because the low molecular weight component in the amorphous polyester reacts only with one of the tin compound or titanium compound. It is thought that the improvement in the hot offset resistance and fixing wraparound resistance is then not obtained as a result.

The addition of these tin compound and titanium compound as a catalyst for the synthesis of the amorphous polyester by the condensation polymerization enables the tin compound and titanium compound to be uniformly dispersed in the amorphous polyester and thus is most preferred from the standpoint of enabling the effective development of the crosslinking reactions during toner production. That is, the tin compound and titanium compound are preferably derived from the catalysts used in the synthesis of the amorphous polyester.

Or, an amorphous polyester containing a tin compound and titanium compound may also be obtained by adding and mixing the tin compound and/or titanium compound after the amorphous polyester has already been produced.

Organotin compounds and inorganic tin compounds are preferred as tin compounds preferred for use in the present invention. Specific examples are organotin compounds such as dibutyltin dichloride, dibutyltin oxide, and diphenyltin oxide. Here, an organotin compound indicates a compound that contains the Sn—C bond.

Inorganic tin compounds, which do not contain the Sn—C bond, are also preferred for use. Here, an inorganic tin compound indicates a compound that does not contain the Sn—C bond. Inorganic tin compounds can be exemplified by tin unbranched alkylcarboxylates such as tin diacetate, tin dihexanoate, tin dioctanoate, and tin distearate; tin branched alkylcarboxylates such as tin dineopentanoate and tin di(2-ethylhexanoate); tin carboxylates such as tin oxalate; and dialkoxytins such as dioctyloxytin and distearoxytin. Preferred among these tin compounds are tin alkylcarboxylates and dialkoxytins, while tin alkylcarboxylates, which have a carboxy residue in the molecule, e.g., tin dioctanoate, tin di(2-ethylhexanoate), and tin distearate, are particularly preferred.

The aforementioned inorganic tin compounds have, within each molecule, a plurality of sites that react with the carboxy group. As a result they are particularly preferred in order to more effectively bring about the crosslinking reactions of the low molecular weight component of the amorphous polyester.

Titanium compounds preferred for use in the present invention can be exemplified by titanium alkoxides, titanium aromatic carboxylate compounds, and titanium compounds having a residue derived from alkanolamine.

The following compounds are provided as specific examples. Examples of titanium alkoxides are tetraethyl titanate, tetrapropyl titanate, tetraisopropyl titanate, tetra(n-butyl) titanate, tetraoctyl titanate, and tetrastearyl titanate.

In addition, the crosslinking reaction with the hydroxy group in the low molecular weight component of the amorphous polyester also proceeds readily with titanium aromatic carboxylate compounds, such as the following, and their use is thus preferred. Examples are titanium phthalate, titanium isophthalate, titanium terephthalate, titanium trimellitate, titanium pyromellitate, titanium 1,3-naphthalenedicarboxylate, titanium 2,4,6-naphthalenetricarboxylate, and titanium salicylate.

The titanium aromatic carboxylate compound is preferably the reaction product of an aromatic carboxylic acid and a titanium alkoxide. The aromatic carboxylic acid is more preferably an at least dibasic aromatic carboxylic acid (that is, the aromatic carboxylic acid has at least two carboxy groups) and/or aromatic oxycarboxylic acid. The at least dibasic aromatic carboxylic acid can be exemplified by dicarboxylic acids such as phthalic acid, isophthalic acid, and terephthalic acid and their anhydrides, and by polybasic carboxylic acids such as trimellitic acid, pyromellitic acid, benzophenonedicarboxylic acid, benzophenonetetracarboxylic acid, naphthalenedicarboxylic acid, naphthalenetricarboxylic acid, and naphthalenetetracarboxylic acid and their anhydrides and esters. The aforementioned aromatic oxycarboxylic acid can be exemplified by salicylic acid, m-oxybenzoic acid, p-oxybenzoic acid, gallic acid, mandelic acid, and tropic acid. Among the preceding, the use of an at least dibasic carboxylic acid as the aromatic carboxylic acid is more preferred, while the use of isophthalic acid, terephthalic acid, trimellitic acid, and naphthalenedicarboxylic acid is particularly preferred.

Titanium compounds having an alkanolamine-derived residue in the molecule also have a high reactivity with the hydroxy group in the polyester low molecular weight component and their use is thus more preferred. Examples are titanium tetrakis(monoethanolaminate), titanium monohydroxytris(triethanolaminate), titanium dihydroxybis(triethanolaminate), titanium trihydroxytriethanolaminate, titanium dihydroxybis(diethanolaminate), titanium dihydroxybis (monoethanolaminate), titanium dihydroxybis(monopropanolaminate), titanium dihydroxybis(N-methyldiethanolaminate), titanium dihydroxybis(N-butyldiethanolaminate), the reaction product of tetrahydroxytitanium and N,N,N',N'- tetrahydroxyethylethylenediamine, titanylbis(triethanolaminate), titanylbis(diethanolaminate), titanylbis(monoethanolaminate), titanylhydroxytriethanolaminate, titanylisopropoxytriethanolaminate, and the intramolecular or intermolecular polycondensates of the preceding.

These titanium compounds can be obtained in a stable manner by, for example, reacting a commercially available titanium dialkoxybis(alcoholaminate, e.g., from DuPont) at 70° C. to 90° C. in the presence of water. The polycondensate can be obtained by the additional removal of the water of condensation at 100° C. by distillation under reduced pressure.

The following are more preferred among these titanium compounds: titanium alkoxides such as tetrapropyl titanate, tetraisopropyl titanate, tetra(n-butyl) titanate, and tetraoctyl titanate; titanium aromatic carboxylate compounds such as titanium isophthalate, titanium terephthalate, titanium trimellitate, and titanium pyromellitate; and titanium dihydroxybis(triethanolaminate), titanium dihydroxybis(diethanolaminate), titanium monohydroxytris(triethanolaminate), titanium tetrakis(monoethanolaminate), titanyl hydroxytriethanolaminate, titanylbis(triethanolaminate), and the intramolecular and intermolecular polycondensates of the preceding.

The aforementioned titanium compounds have, within each molecule, a plurality of sites that react with the hydroxy group. As a result they are particularly preferred in order to more effectively bring about the crosslinking reactions of the low molecular weight component of the amorphous polyester.

It is critical for the present invention that the abundance ratio Sn/Ti of the element tin and the element titanium in the amorphous polyester be 20/80 to 80/20. When the range for Sn/Ti is the indicated range, the crosslinking reactions of the low molecular weight component in the amorphous polyester then proceed with good efficiency and molecules with more extensively crosslinked structures are obtained and the effects of the invention are obtained. 30/70 to 70/30 is more preferred from the standpoint of improving the charge stability and because this provides an even more facile development of the crosslinking reactions. The crosslinking reactions do not develop adequately at below 20/80 and above 80/20 and the effects of the present invention cannot then be obtained.

The following methods are examples of methods for adjusting the Sn/Ti range. The amorphous polyester 1 can be produced using a tin compound as described above as a catalyst and the amorphous polyester 2 can be produced using a titanium compound as described above. And then, one example is to change the mass ratio between the amorphous polyester 1 and the amorphous polyester 2 used in toner production.

Another example is to change the mass of the tin compound and/or titanium compound used as catalysts for synthesis of the amorphous polyester.

In addition, after the amorphous polyester has been produced using a tin compound or titanium compound as described above, the other compound can be added and mixed so as to provide the Sn/Ti range of the present invention and thereby obtain amorphous polyester containing a tin compound and titanium compound.

The total abundance of the element tin and the element titanium with respect to the overall amorphous polyester is preferably 50 to 20,000 ppm on a mass basis. At 50 ppm and above, the crosslinking reaction readily progresses and the improvements in the hot offset resistance and fixing wraparound resistance are readily obtained. On the other hand, the charging performance is enhanced at 20,000 ppm and below. 200 to 5,000 ppm is more preferred.

The constitution of the toner of the present invention is described in detail in the following.

(Amorphous Polyester)

Common amorphous polyesters constituted of an alcohol component and an acid component can be used as the amorphous polyester, and examples of both components are provided below.

The alcohol component can be exemplified by ethylene glycol, propylene glycol, 1,3-butanediol, 1,4-butanediol, 2,3-butanediol, diethylene glycol, triethylene glycol, 1,5-pentanediol, 1,6-hexanediol, neopentyl glycol, 2-ethyl-1,3-hexanediol, cyclohexanedimethanol, butenediol, octenediol, cyclohexenedimethanol, hydrogenated bisphenol A, and bisphenol derivatives given by formula (1) below. Bisphenols such as hydrogenated bisphenol A and the bisphenol derivatives given by formula (1) below, and aromatic polyhydric alcohols including 1,2-benzenedimethanol and 1,4-benzenedimethanol and their derivatives are preferred, while bisphenols such as hydrogenated bisphenol A and the bisphenol derivatives given by formula (1) below are more preferred.

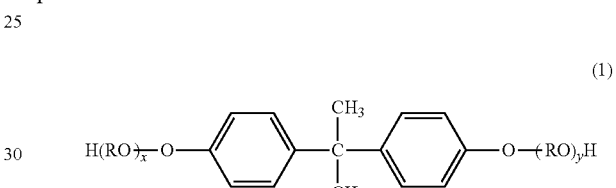

(1)

[In the formula, R is an ethylene group or propylene group; x and y are each integers equal to or greater than 0; and the average value of x+y is 1 to 10.]

The alcohol component can also be exemplified by polyhydric alcohols such as glycerin, pentaerythritol, sorbitol, sorbitan, and the oxyalkylene ethers of novolac-type phenolic resins.

On the other hand, the dibasic carboxylic acids constituting the amorphous polyester can be exemplified by benzenedicarboxylic acids and their anhydrides, e.g., phthalic acid, terephthalic acid, isophthalic acid, and phthalic anhydride, and by alkyldicarboxylic acids, e.g., succinic acid, adipic acid, sebacic acid, and azelaic acid, and their anhydrides. Additional examples are succinic acid substituted by a $C_{6-18}$ alkyl group or alkenyl group, and anhydrides thereof, and unsaturated dicarboxylic acids, e.g., fumaric acid, maleic acid, citraconic acid, and itaconic acid, and their anhydrides. Other examples are polybasic carboxylic acids, e.g., trimellitic acid, pyromellitic acid, 1,2,3,4-butanetetracarboxylic acid, and benzophenonetetracarboxylic acid, and their anhydrides.

The amorphous polyester (preferably the amorphous polyester 1 and more preferably the amorphous polyesters 1 and 2) in the present invention preferably is the polycondensate of a carboxylic acid component and an alcohol component that contains at least 80 mol % (more preferably at least 90 mol % and not more than 100 mol %) of an aromatic polyhydric alcohol (more preferably the bisphenols). By having the alcohol component contain the bisphenols as its major component, the reactivity with the titanium compound present in the amorphous polyester is increased and the fixing wraparound resistance is further enhanced.

An "other catalyst" as commonly used in polyester production may be used to produce the aforementioned amorphous polyester, for example, a metal such as antimony, aluminum, manganese, nickel, zinc, lead, iron, magnesium, calcium, and germanium, or a compound that contains such a metal. When this other catalyst is used by itself, the aforementioned tin compound and titanium compound are used for toner production through their addition and mixture after production of the amorphous polyester.

Here, in order for the crosslinking reactions mediated by the tin compound and titanium compound to be effectively expressed, the tin compound and titanium compound preferably are added at at least 0.01 mass parts and not more than 2 mass parts per 100 mass parts of the amorphous polyester. Moreover, viewed in terms of enabling a more reliable expression of the effects of the present invention, the addition of at least 5-fold on a mass parts basis with respect to the mass parts of the "other catalyst" used for amorphous polyester production is preferred.

Viewed from the standpoint of the charge stability, the acid value of the amorphous polyester is preferably at least 1 mg KOH/g and not more than 40 mg KOH/g and is more preferably at least 1 mg KOH/g and not more than 15 mg KOH/g.

The amorphous polyester characteristically comprises an amorphous polyester 1 for which the weight-average molecular weight Mw1 as measured by gel permeation chromatography (GPC) is Mw1<7,000.

By having the weight-average molecular weight Mw1 of the amorphous polyester 1 by GPC measurement be Mw1<7,000, the toner then has a sharp melt property and a toner having an excellent low-temperature fixability is provided. Moreover, due to the content of a relatively low molecular weight component having a molecular weight of not more than 2,000, the molecular weight is raised through reaction with and crosslinking by the tin compound and titanium compound and a toner can be provided that has an excellent hot offset resistance and an excellent fixing wraparound resistance. The low-temperature fixability declines and coexistence between the hot offset resistance and fixing wraparound resistance is strongly impaired when Mw1 is at least 7,000.

In addition, preferably Mw1 is at least 3,000 from the standpoint of toner storability. A more preferred range for Mw1 is 3,500<Mw1<6,500. Mw1 can be controlled using, for example, the amounts of alcohol component and acid component charged during production, the reaction temperature, and the reaction time.

The glass transition temperature of the amorphous polyester 1 is preferably at least 40° C. and not more than 65° C. and is more preferably at least 50° C. and not more than 60° C., considered from the standpoint of the coexistence of the toner storability with the low-temperature fixability.

The softening point of the amorphous polyester 1 is preferably at least 75° C. and not more than 120° C. considered from the standpoint of the coexistence of the toner storability with the low-temperature fixability.

The amorphous polyester used in the toner of the present invention may contain an amorphous polyester 2 in addition to the amorphous polyester 1.

The hot offset resistance and the fixing wraparound resistance are further improved when the weight-average molecular weight Mw2 of the amorphous polyester 2 as measured by gel permeation chromatography (GPC) is Mw2<7,000, and this is thus preferred. A more preferred range for Mw2 is 3,500<Mw2<6,500. Mw2 can be controlled using, for example, the amounts of alcohol component and acid component charged during production, the reaction temperature, and the reaction time.

Amorphous polyesters 1 and 2 preferably contain at least one selection from tin compounds and titanium compounds. For example, preferably amorphous polyester 1 contains a titanium compound and amorphous polyester 2 contains a tin compound.

The amorphous polyester used in the toner of the present invention may contain additional amorphous polyester besides the amorphous polyester 1 and amorphous polyester 2.

The proportion of the amorphous polyester 1, which has a weight-average molecular weight Mw by GPC of less than 7,000, is preferably at least 50 mass parts per 100 mass parts of the total amorphous polyester because this provides a large amount of low molecular weight component in the amorphous polyester and the crosslinking reaction progresses further.

(Other Binder Resin)

The toner of the present invention contains amorphous polyester as the binder resin. With the goals of enhancing the dispersibility of the pigment and improving the charge stability of the toner and its blocking resistance, an "other resin" as described below may also be added, in addition to the aforementioned amorphous polyester, in an amount that does not impair the effects of the present invention.

The following resins are examples of this "other resin": homopolymers of styrene and its derivatives such as polystyrene, poly-p-chlorostyrene, and polyvinyltoluene; styrenic copolymers such as styrene-p-chlorostyrene copolymer, styrene-vinyltoluene copolymer, styrene-vinylnaphthalene copolymer, styrene-acrylate ester copolymer, styrene-methacrylate ester copolymer, styrene-methyl α-chloromethacrylate copolymer, styrene-acrylonitrile copolymer, styrene-vinyl methyl ether copolymer, styrene-vinyl ethyl ether copolymer, styrene-vinyl methyl ketone copolymer, and styrene-acrylonitrile-indene copolymer; as well as polyvinyl chloride, phenolic resins, natural resin-modified phenolic resins, natural resin-modified maleic acid resins, acrylic resins, methacrylic resins, polyvinyl acetate resins, silicone resins, polyester resins, polyurethane, polyamide resins, furan resins, epoxy resins, xylene resins, polyvinyl butyral, terpene resins, coumarone-indene resins, and petroleum resins.

(Colorant)

A colorant may be used in the toner of the present invention. This colorant can be exemplified by the following.

The black colorant can be exemplified by carbon black and by black colorants provided by color mixing using a yellow colorant, magenta colorant, and cyan colorant to yield a black color. While a pigment may be used by itself for the colorant, improving the sharpness through the co-use of a dye and a pigment is more preferred from the standpoint of the image quality of the full-color image.

Pigments for magenta toners can be exemplified by the following: C.I. Pigment Red 1, 2, 3, 4, 5, 6, 7, 8, 9, 10, 11, 12, 13, 14, 15, 16, 17, 18, 19, 21, 22, 23, 30, 31, 32, 37, 38, 39, 40, 41, 48:2, 48:3, 48:4, 49, 50, 51, 52, 53, 54, 55, 57:1, 58, 60, 63, 64, 68, 81:1, 83, 87, 88, 89, 90, 112, 114, 122, 123, 146, 147, 150, 163, 184, 202, 206, 207, 209, 238, 269, and 282; C.I. Pigment Violet 19; and C.I. Vat Red 1, 2, 10, 13, 15, 23, 29, and 35.

Dyes for magenta toners can be exemplified by the following: oil-soluble dyes such as C.I. Solvent Red 1, 3, 8, 23, 24, 25, 27, 30, 49, 81, 82, 83, 84, 100, 109, and 121, C.I. Disperse Red 9, C.I. Solvent Violet 8, 13, 14, 21, and 27, and C.I. Disperse Violet 1; and basic dyes such as C.I. Basic Red 1, 2, 9, 12, 13, 14, 15, 17, 18, 22, 23, 24, 27, 29, 32, 34, 35, 36, 37, 38, 39, and 40, and C.I. Basic Violet 1, 3, 7, 10, 14, 15, 21, 25, 26, 27, and 28.

Pigments for cyan toners can be exemplified by the following: C.I. Pigment Blue 2, 3, 15:2, 15:3, 15:4, 16, and 17; C.I. Vat Blue 6; C.I. Acid Blue 45; and copper phthalocyanine pigments having at least 1 and not more than 5 phthalimidomethyl groups substituted on the phthalocyanine skeleton.

C.I. Solvent Blue 70 is an example of a dye for cyan toners.

Pigments for yellow toners can be exemplified by the following: C.I. Pigment Yellow 1, 2, 3, 4, 5, 6, 7, 10, 11, 12, 13, 14, 15, 16, 17, 23, 62, 65, 73, 74, 83, 93, 94, 95, 97, 109, 110, 111, 120, 127, 128, 129, 147, 151, 154, 155, 168, 174, 175, 176, 180, 181, and 185; and C.I. Vat Yellow 1, 3, and 20.

C.I. Solvent Yellow 162 is an example of a dye for yellow toners.

The content of the colorant is preferably at least 0.1 mass parts and not more than 30 mass parts per 100 mass parts of the binder resin. The binder resin here denotes the total of the amorphous polyester and the aforementioned "other resins".

(Wax)

A wax may be used in the toner of the present invention. This wax can be exemplified by the following: hydrocarbon waxes such as low molecular weight polyethylene, low molecular weight polypropylene, alkylene copolymers, microcrystalline wax, paraffin wax, and Fischer-Tropsch waxes; oxides of hydrocarbon waxes, such as oxidized polyethylene wax, and their block copolymers; waxes in which the major component is fatty acid ester, such as carnauba wax; and waxes provided by the partial or complete deacidification of fatty acid esters, such as deacidified carnauba wax.

Additional examples are as follows: saturated straight-chain fatty acids such as palmitic acid, stearic acid, and montanic acid; unsaturated fatty acids such as brassidic acid, eleostearic acid, and parinaric acid; saturated alcohols such as stearyl alcohol, aralkyl alcohols, behenyl alcohol, carnaubyl alcohol, ceryl alcohol, and melissyl alcohol; polyhydric alcohols such as sorbitol; esters between fatty acids such as palmitic acid, stearic acid, behenic acid, and montanic acid and alcohols such as stearyl alcohol, aralkyl alcohols, behenyl alcohol, carnaubyl alcohol, ceryl alcohol, and melissyl alcohol; fatty acid amides such as linoleamide, oleamide, and lauramide; saturated fatty acid bisamides such as methylenebisstearamide, ethylenebiscapramide, ethylenebislauramide, and hexamethylenebisstearamide; unsaturated fatty acid amides such as ethylenebisoleamide, hexamethylenebisoleamide, N,N'-dioleyladipamide, and N,N'-dioleylsebacamide; aromatic bisamides such as m-xylenebisstearamide and N,N'-distearylisophthalamide; fatty acid metal salts (generally known as metal soaps) such as calcium stearate, calcium laurate, zinc stearate, and magnesium stearate; waxes provided by grafting an aliphatic hydrocarbon wax using a vinylic monomer such as styrene or acrylic acid; partial esters between a polyhydric alcohol and a fatty acid, such as behenic monoglyceride; and hydroxy group-containing methyl ester compounds obtained by the hydrogenation of plant oils.

Among these waxes, hydrocarbon waxes such as paraffin waxes and Fischer-Tropsch waxes and fatty acid ester waxes such as carnauba wax are preferred from the standpoint of bringing about additional improvements in the hot offset resistance. Hydrocarbon waxes are more preferred and Fischer-Tropsch waxes are still more preferred in the present invention from the standpoint of the hot offset resistance being further improved.

The wax content is preferably at least 1 mass part and not more than 20 mass parts per 100 mass parts of the binder resin.

The peak temperature of the maximum endothermic peak of the wax in the endothermic curve measured during ramp up in measurement with a differential scanning calorimeter (DSC) is preferably at least 45° C. and not more than 140° C. and is more preferably at least 70° C. and not more than 105° C. The toner storability can coexist with the hot offset resistance when the peak temperature of the maximum endothermic peak of the wax is in the indicated range, which is thus preferred.

(Charge Control Agent)

A charge control agent may as necessary also be incorporated in the toner of the present invention. While a known charge control agent can be used as the charge control agent incorporated in the toner, in particular it is preferably a metal compound of an aromatic carboxylic acid that is colorless, supports a rapid charging speed of the toner, and enables the stable maintenance of a certain charge quantity.

Negative-charging charge control agents can be exemplified by metal salicylate compounds, metal naphthoate compounds, metal dicarboxylate compounds, polymeric compounds having sulfonic acid or carboxylic acid in side chain position, polymeric compounds having sulfonate salt or sulfonate ester in side chain position, polymeric compounds having carboxylate salt or carboxylate ester in side chain position, boron compounds, urea compounds, silicon compounds, and calixarene. Positive-charging charge control agents can be exemplified by quaternary ammonium salts, polymeric compounds having a quaternary ammonium salt in side chain position, guanidine compounds, and imidazole compounds. The charge control agent may be internally added or externally added to the toner particle. The amount of addition of the charge control agent is preferably at least 0.2 mass parts and not more than 10 mass parts per 100 mass parts of the binder resin.

(Inorganic Fine Powder)

An additional inorganic fine powder may as necessary also be contained in the toner of the present invention. The inorganic fine powder may be internally added to the toner particle or may be mixed with the toner particle as an external additive. Inorganic fine powders such as those of silica, titanium oxide, and aluminum oxide are preferred as the external additive. The inorganic fine powder preferably is hydrophobed using a hydrophobic agent such as a silane compound, silicone oil, or mixture thereof.

An inorganic fine powder having a specific surface area of at least 50 $m^2/g$ and not more than 400 $m^2/g$ is preferred as an external additive for improving the flowability, while an inorganic fine powder having a specific surface area of at least 10 $m^2/g$ and not more than 50 $m^2/g$ is preferred for stabilizing the durability. Combinations of inorganic fine powders having specific surface areas in the indicated ranges may be used in order to have the flowability coexist with the stabilization of the durability.

The external additive is preferably used at at least 0.1 mass parts and not more than 10.0 mass parts per 100 mass parts of the toner particle. Mixing of the toner particle with the external additive can use a known mixer such as a Henschel mixer.

<Developer>

The toner of the present invention can be used as a single-component developer, but use mixed with a magnetic carrier as a two-component developer is preferred in order to bring about additional improvements in the dot reproducibility and also from the standpoint of obtaining a stable image on a long-term basis.

A generally known magnetic carrier can be used, for example, surface-oxidized iron powder and unoxidized iron powder; metal particles such as those of iron, lithium, calcium, magnesium, nickel, copper, zinc, cobalt, manganese, chromium, and rare earths and their alloy particles and oxide particles; magnetic bodies such as ferrite; and magnetic body-dispersed resin carriers (known as resin carriers), which contain a magnetic body and a binder resin that maintains this magnetic body in a dispersed state.

When the toner of the present invention is used mixed with a magnetic carrier as a two-component developer, very good effects are obtained when the carrier mixing ratio here, expressed as the toner concentration in the two-component developer, is made preferably at least 2 mass % and not more than 15 mass % and more preferably at least 4 mass % and not more than 13 mass %.

<Production Method>

Known methods can be used as the method for producing the toner particle, e.g., dry methods such as pulverization methods and wet methods such as emulsion aggregation methods and dissolution suspension methods.

Regardless of the method, preferably the tin compound and titanium compound present in the amorphous polyester and the low molecular weight component in the amorphous polyester are mixed and a step is executed in which the amorphous polyester 1 is heated. In this heating step, heating is particularly preferably carried out to at least the glass transition temperature of the amorphous polyester 1 and more preferably to a temperature that is at least the softening point of the amorphous polyester 1. By doing this, the crosslinking reactions of the low molecular weight component, tin compound, and titanium compound in the amorphous polyester 1 can be efficiently developed and the effects of the present invention can then be more reliably expressed.

In the case of pulverization methods, this can be realized in a step of melt-kneading the amorphous polyester.

In the case of emulsion aggregation methods, this can be realized in the step of preparing a dispersion of fine particles that contain the amorphous polyester or in the step of heating and fusing the aggregate particles.

In the case of dissolution suspension methods, this can be realized in the step of preparing a dispersion of the toner materials that include the amorphous polyester.

Among these, it is easy in a pulverization method that includes a step of melt-kneading the amorphous polyester to apply high shear force while applying high temperatures. Doing this facilitates a more extensive development of the tin compound- and titanium compound-mediated crosslinking reactions of the low molecular weight component of the amorphous polyester and thereby facilitates further improvements in the hot offset resistance and fixing wraparound resistance and is thus particularly preferred.

An example of a toner production procedure using a pulverization method is described in the following.

In a starting material mixing step, the materials constituting the toner particle, for example, the amorphous polyester and optional other components such as other resins, wax, colorant, and charge control agent are weighed out in prescribed amounts and are blended and mixed. The mixing apparatus can be exemplified by the double cone mixer, V-mixer, drum mixer, Supermixer, Henschel mixer, Nauta mixer, and Mechano Hybrid (Nippon Coke & Engineering Co., Ltd.).

The mixed materials are then melt-kneaded to disperse the wax and so forth in the amorphous polyester. The kneading output temperature can be adjusted as appropriate depending on the amorphous polyester used, but generally 100° C. to 180° C. is preferred. A batch kneader, e.g., a pressure kneader and Banbury mixer, or a continuous kneader can be used in this melt-kneading step, and single-screw extruders and twin-screw extruders are the mainstream because they offer the advantage of enabling continuous production.

Examples here are the KTK twin-screw extruder (Kobe Steel, Ltd.), TEM twin-screw extruder (Toshiba Machine Co., Ltd.), PCM kneader (Ikegai Corp), Twin Screw Extruder (KCK), Co-Kneader (Buss AG), and Kneadex (Nippon Coke & Engineering Co., Ltd.). In addition, the resin composition provided by melt-kneading may be rolled out using, e.g., a two-roll mill, and may be cooled in a cooling step using, e.g., water.

The cooled resin composition is then pulverized to the desired particle diameter in a pulverization step. In the pulverization step, a coarse pulverization is performed using a grinder, e.g., a crusher, hammer mill, or feather mill, followed by a fine pulverization using a pulverizer such as a Kryptron System (Kawasaki Heavy Industries, Ltd.), Super Rotor (Nisshin Engineering Inc.), or Turbo Mill (Freund-Turbo Corporation) or using an air jet system.

A classified product (toner particle) is subsequently obtained as necessary by carrying out classification using a sieving apparatus or a classifier, e.g., an internal classification system such as the Elbow Jet (Nittetsu Mining Co., Ltd.) or a centrifugal classification system such as the Turboplex (Hosokawa Micron Corporation), TSP Separator (Hosokawa Micron Corporation), or Faculty (Hosokawa Micron Corporation). Among the preceding, the Faculty (Hosokawa Micron Corporation) can carry out a spherizing treatment of the toner particle at the same time as classification and is thus preferred from the standpoint of improving the transfer efficiency.

After pulverization, the toner particle may as necessary also be subjected to a surface treatment, such as a spherizing treatment, using a Hybridization System (Nara Machinery Co., Ltd.), Mechanofusion System (Hosokawa Micron Corporation), Faculty (Hosokawa Micron Corporation), or Meteo Rainbow MR Type (Nippon Pneumatic Mfg. Co., Ltd.).

The average circularity of the toner is preferably at least 0.930 and not more than 0.985 from the standpoint of having the cleaning performance coexist with an improved transferability. When the toner is produced by a pulverization method, a surface treatment, e.g., a spherizing treatment or heat treatment, is preferably carried out on the toner particle in order to produce a toner having the indicated average circularity.

As necessary, the surface of the toner particle is additionally subjected to an external addition treatment with an external additive. The method for carrying out the external addition treatment with the external additive can be exemplified by blending a prescribed amount of any of various known external additives with the classified toner and stirring and mixing using as the external addition device a mixing apparatus such as a double cone mixer, V-mixer, drum mixer, Supermixer, Henschel mixer, Nauta mixer, Mechano Hybrid (Nippon Coke & Engineering Co., Ltd.), or Nobilta (Hosokawa Micron Corporation).

The methods used to measure the various properties of the toner and starting materials are described in the following.

<Sn/Ti Abundance Ratio by x-Ray Fluorescence Analysis of the Sn and Ti Present in the Amorphous Polyester>

The Sn/Ti abundance ratio for the Sn and Ti is determined by x-ray fluorescence. The x-ray fluorescence is measured based on JIS K 0119-1969 and specifically is according to the following.

The following are used as the measurement instrumentation: an "Axios" (PANalytical B.V.) wavelength-dispersive x-ray fluorescence analyzer and the "SuperQ ver. 4.0F" (PANalytical B.V.) dedicated software supplied therewith for setting the measurement conditions and analyzing the measurement data. Rh is used for the anode of the x-ray tube; a vacuum is used for the measurement atmosphere; 27 mm is used for the measurement diameter (collimator mask diameter); and 10 seconds is used for the measurement time. A known detector, e.g., a proportional counter (PC) and scintillation counter (SC), can be used for the detector.

4 g of the sample is introduced into a dedicated aluminum press ring and smoothed over and is molded into a pellet having a thickness of 2 mm and a diameter of 39 mm by compression for 60 seconds at 20 MPa using a "BRE-32" tablet compression molder (Maekawa Testing Machine Mfg. Co., Ltd.) to produce a pellet that is used as the measurement sample.

Samples for constructing the calibration curves are first prepared. A known amount of tin oxide is added to and mixed with 100 mass parts of a styrene powder that contains neither the element tin nor the element titanium, followed by preparation of the pellet for the element tin. Similarly, a known amount of titanium oxide is added to and mixed with 100 mass parts of a styrene powder that contains neither the element tin nor the element titanium, followed by preparation of the measurement pellet for measurement of the element titanium.

Each of the prepared pellets is measured with the x-ray fluorescence analyzer and calibration curves are constructed for tin and titanium from the peak intensities obtained for the individual samples for the tin oxide or titanium oxide in the styrene powder.

A sample of the amorphous polyester used in the present invention is then measured with the x-ray fluorescence analyzer and the tin content and titanium content are determined by comparing the obtained peak intensities with the calibration curves, and the resulting values are used to determine the Sn/Ti abundance ratio for the Sn and Ti.

When a plurality of amorphous polyesters are used, the tin content and titanium content are determined for each amorphous polyester used and the Sn/Ti of the amorphous polyester is calculated from the content proportions for the plurality of amorphous polyesters.

<Method for Measuring the Weight-Average Molecular Weight (Mw) by GPC>

The weight-average molecular weight (Mw) is measured as follows using gel permeation chromatography (GPC).

First, the sample (resin) is dissolved in tetrahydrofuran (THF) over 24 hours at room temperature. The obtained solution is filtered across a "Sample Pretreatment Cartridge" solvent-resistant membrane filter with a pore diameter of 0.2 μm (Tosoh Corporation) to obtain the sample solution. The sample solution is adjusted to a THF-soluble component concentration of approximately 0.8 mass %. The measurement is performed under the following conditions using this sample solution.

instrument: HLC8120 GPC (detector: RI) (Tosoh Corporation)
columns: 7-column train of Shodex KF-801, 802, 803, 804, 805, 806, and 807 (Showa Denko Kabushiki Kaisha)
eluent: tetrahydrofuran (THF)
flow rate: 1.0 mL/minute
oven temperature: 40.0° C.
sample injection amount: 0.10 mL A molecular weight calibration curve constructed using polystyrene resin standards (for example, product name "TSK Standard Polystyrene F-850, F-450, F-288, F-128, F-80, F-40, F-20, F-10, F-4, F-2, F-1, A-5000, A-2500, A-1000, and A-500", Tosoh Corporation) is used to determine the molecular weight of the sample.

<Method for Measuring the Softening Point of the Resins>

The softening point of the resins is measured according to the manual provided with the instrument, using a "Flowtester CFT-500D Flow Property Evaluation Instrument" (Shimadzu Corporation), which is a constant-load extrusion-type capillary rheometer. With this instrument, while a constant load is applied by a piston from the top of the measurement sample, the measurement sample filled in a cylinder is heated and melted and the melted measurement sample is extruded from a die at the bottom of the cylinder; a flow curve showing the relationship between piston stroke and temperature is obtained from this.

The "melting temperature by the ½ method", as described in the manual provided with the indicated instrument, is used as the softening point in the present invention. The melting temperature by the ½ method is determined proceeding as follows. First, the value of X—i.e., ½ of the difference between Smax, which is the piston stroke at the completion of outflow, and Smin, which is the piston stroke at the start of outflow—is determined (X=(Smax−Smin)/2). The temperature of the flow curve when the piston stroke in the flow curve reaches "Smin+X" is the melting temperature by the ½ method.

The measurement sample used is prepared by subjecting approximately 1.0 g of the resin to compression molding for approximately 60 seconds at approximately 10 MPa in a 25° C. environment using a tablet compression molder (for example, NT-100H, NPa System Co., Ltd.) to provide a cylindrical shape having a diameter of approximately 8 mm.

The measurement conditions with the CFT-500D are as follows.
test mode: rising temperature method
start temperature: 50° C.
saturated temperature: 200° C.
measurement interval: 1.0° C.
ramp rate: 4.0° C./minute
piston cross section area: 1.000 cm$^2$
test load (piston load): 10.0 kgf (0.9807 MPa)
preheating time: 300 seconds
diameter of die orifice: 1.0 mm
die length: 1.0 mm <Method for Measuring the Acid Value of the Resins>

The acid value of the polyester resin is measured by the following method. The acid value is the number of milligrams of potassium hydroxide required to neutralize the acid present in 1 g of a sample. The acid value of the polyester resin is measured in accordance with JIS K 0070-1992. In specific terms it is measured according to the following procedure.

(1) Reagent Preparation

A phenolphthalein solution is obtained by dissolving 1.0 g of phenolphthalein in 90 mL of ethyl alcohol (95 volume %) and bringing to 100 mL by adding deionized water. 7 g of special-grade potassium hydroxide is dissolved in 5 mL of deionized water and this is brought to 1 L by the addition of ethyl alcohol (95 volume %). This is introduced into an alkali-resistant container avoiding contact with, for example, carbon dioxide, and allowed to stand for 3 days, after which time filtration is carried out to obtain a potassium hydroxide solution. The obtained potassium hydroxide solution is stored in an alkali-resistant container. The factor for this potassium hydroxide solution is determined from the amount of the potassium hydroxide solution required for neutralization when 25 mL of 0.1 mol/L hydrochloric acid is introduced into an Erlenmeyer flask, several drops of the aforementioned phenolphthalein solution are added, and titration is performed using the potassium hydroxide solution. The 0.1 mol/L hydrochloric acid used is prepared in accordance with JIS K 8001-1998.

(2) Procedure (A) Main Test 2.0 g of a sample of the pulverized polyester resin is exactly weighed into a 200-mL Erlenmeyer flask and 100 mL of a toluene:ethanol (2:1) mixed solution is added and dissolution is carried out over 5 hours. Several drops of the aforementioned phenolphthalein solution are added as indicator and titration is performed using the aforementioned potassium hydroxide solution. The titration endpoint is taken to be persistence of the faint pink color of the indicator for approximately 30 seconds.

(B) Blank Test

The same titration as in the above procedure is run, but without using the sample (that is, with only the toluene:ethanol (2:1) mixed solution).

(3) The acid value is calculated by substituting the obtained results into the following formula.

$$A=[(C-B)\times f\times 5.61]/S$$

Here, A: acid value (mg KOH/g); B: amount (mL) of addition of the potassium hydroxide solution in the blank test; C: amount (mL) of addition of the potassium hydroxide solution in the main test; f: factor for the potassium hydroxide solution; and S: sample (g).

<Method for Measuring the Glass Transition Temperature of the Resins>

The glass transition temperature of the resins is measured based on ASTM D 3418-82 using a "Q1000" differential scanning calorimeter (TA Instruments). Temperature correction in the instrument detection section is performed using the melting points of indium and zinc, and the amount of heat is corrected using the heat of fusion of indium.

Specifically, approximately 5 mg of the resin is exactly weighed out and this is introduced into an aluminum pan, and the measurement is run at a ramp rate of 10° C./minute in the measurement temperature range between 30° C. and 200° C. using an empty aluminum pan as reference. The measurement is carried out by initially raising the temperature of the resin to 200° C., holding for 10 minutes, then cooling to 30° C., and subsequently reheating. The change in the specific heat in the temperature range of 35° C. to 100° C. in this second heating step is obtained. Here, the glass transition temperature (Tg) of the resin is taken to be the point at the intersection between the differential heat curve and the line for the midpoint for the baselines for prior to and subsequent to the appearance of the change in the specific heat.

<Method for Measuring the Peak Temperature of the Maximum Endothermic Peak of the Waxes>

The peak temperature of the maximum endothermic peak of the waxes is measured based on ASTM D 3418-82 using a "Q1000" differential scanning calorimeter (TA Instruments). Temperature correction in the instrument detection section is performed using the melting points of indium and zinc, and the amount of heat is corrected using the heat of fusion of indium.

Specifically, approximately 10 mg of the wax is exactly weighed out and this is introduced into an aluminum pan, and the measurement is run at a ramp rate of 10° C./minute in the measurement temperature range between 30° C. and 200° C. using an empty aluminum pan as reference. The measurement is carried out by initially raising the temperature of the wax to 200° C., holding for 10 minutes, then cooling to 30° C., and subsequently reheating. The peak temperature of the maximum endothermic peak of the wax is taken to be the temperature that gives the maximum endothermic peak in the DSC curve in the 30° C. to 200° C. temperature range in this second ramp-up process.

<Measurement of the BET Specific Surface Area of the Inorganic Fine Powders>

The BET specific surface area of the inorganic fine powders is measured based in JIS Z 8830 (2001). The specific measurement method is as follows.

A "TriStar 3000 Automatic Specific Surface Area Porosimetry Analyzer" (Shimadzu Corporation), which uses gas adsorption by a constant volume procedure as its measurement methodology, is used as the measurement instrument. The measurement conditions are set and the measurement data is analyzed using "TriStar 3000 Version 4.00", the dedicated software provided with this instrument. A vacuum pump, nitrogen gas line, and helium gas conduit are connected to the instrument. The value calculated using a multipoint BET method and using nitrogen gas as the adsorption gas is used as the BET specific surface area of the inorganic fine powder in the present invention.

The BET specific surface area is calculated proceeding as follows.

First, nitrogen gas is adsorbed to the inorganic fine powder and the equilibration pressure P (Pa) within the sample cell and the amount of nitrogen adsorption Va (mol/g) by the external additive are measured at this point. The adsorption isotherm is obtained using the relative pressure Pr—which is the value provided by dividing the equilibration pressure P (Pa) within the sample cell by the saturation vapor pressure of nitrogen Po (Pa)—for the horizontal axis and using the amount of nitrogen adsorption Va (mol/g) for the vertical axis. The monomolecular layer adsorption amount Vm (mol/g), which is the amount of adsorption required to form a monomolecular layer on the surface of the external additive, is then determined using the BET equation provided below.

$$Pr/Va(1-Pr)=1/(Vm\times C)+(C-1)\times Pr/(Vm\times C)$$

Here, C is the BET parameter and is a variable that changes with the type of measurement sample, the type of adsorption gas, and the adsorption temperature.

The BET equation can be rendered as a straight line, with a slope of $(C-1)/(Vm\times C)$ and an intercept of $1/(Vm\times C)$, by using Pr for the x-axis and $Pr/Va(1-Pr)$ for the y-axis. This straight line is called a BET plot.

slope of the straight line=$(C-1)/(Vm\times C)$ intercept of the straight line=$1/(Vm\times C)$ The value of the slope of this straight line and the value of its intercept can be calculated by plotting the measured values of Pr and the measured values of $Pr/Va(1-Pr)$ on a graph and generating a straight line by the least-squares method. Vm and C can be calculated by substituting these values into the aforementioned equations and solving the obtained simultaneous equations.

The BET specific surface area S (m$^2$/g) of the inorganic fine powder is then calculated using the following equation and the Vm calculated as above and the molecular cross-sectional area of the nitrogen molecule (0.162 nm$^2$).

$$S = Vm \times N \times 0.162 \times 10^{-18}$$

Here, N is Avogadro's number (mol$^{-1}$).

Measurements using this instrument are run according to the "TriStar 3000 Operating Manual V4.0" provided with the instrument and specifically are run using the following procedure.

The glass sample cell (stem diameter=⅜ inch, volume=approximately 5 mL) provided with the instrument is thoroughly cleaned and dried and then exactly weighed to determine the tare mass. Approximately 0.1 g of the external additive is introduced into this sample cell using a funnel.

The sample cell loaded with the inorganic fine powder is set in a "Vacuprep 061 Pretreatment Apparatus" (Shimadzu Corporation) connected to a vacuum pump and nitrogen gas line and vacuum degassing is continued for approximately 10 hours at 23° C. This vacuum degassing is performed by gradually degassing while adjusting the valve in order to avoid suctioning the inorganic fine powder into the vacuum pump. The pressure in the sample cell gradually drops as degassing proceeds and approximately 0.4 Pa (approximately 3 millitorr) is finally reached. After the completion of vacuum degassing, nitrogen gas is gradually introduced into the sample cell and the interior of the sample cell is returned to atmospheric pressure and the sample cell is removed from the pretreatment apparatus. The mass of this sample cell is exactly weighed and the precise mass of the external additive is calculated from the difference from the tare mass. The sample cell is closed with a rubber stopper during weighing in order to prevent the external additive in the sample cell from being contaminated with, for example, moisture in the atmosphere.

The "isothermal jacket" provided with the instrument is then installed on the stem of this sample cell loaded with the inorganic fine powder. The filler rod provided with the instrument is inserted into the sample cell and the sample cell is set in the analysis port of the instrument. This isothermal jacket is a cylindrical element whose inside is composed of a porous material and whose outside is composed of an impermeable material, and it can draw up the liquid nitrogen by capillary phenomena to a prescribed level.

Measurement of the free space in the sample cell including the connection fixtures is then performed. For the free space, the volume of the sample cell is measured at 23° C. using helium gas; then, after the sample cell has been cooled with liquid nitrogen, the volume of the sample cell is similarly measured using helium gas; and the free space is calculated converting from the difference in these volumes. In addition, the saturation vapor pressure Po (Pa) of nitrogen is automatically measured separately using the Po tube built into the instrument.

Then, after the interior of the sample cell has been vacuum degassed, the sample cell is cooled with liquid nitrogen while vacuum degassing is continued. After this, nitrogen gas is admitted in stages into the sample cell and the nitrogen molecules are adsorbed to the inorganic fine powder. At this point, the above-described adsorption isotherm is obtained by measurement of the equilibration pressure P (Pa) as required, and this adsorption isotherm is converted to a BET plot. The relative pressure Pr points for data collection are set at a total of six points, i.e., 0.05, 0.10, 0.15, 0.20, 0.25, and 0.30. A straight line is generated by the least-squares method from the obtained measurement data and Vm is calculated from the slope and intercept of this straight line. Using this value of Vm, the BET specific surface area of the inorganic fine powder is calculated as described above.

<Weight-Average Particle Diameter (D4) of the Toner Particle>

Using a "Coulter Counter Multisizer 3" (registered trademark, Beckman Coulter, Inc.), a precision particle size distribution measurement instrument operating on the pore electrical resistance method and equipped with a 100 μm aperture tube, and the accompanying dedicated software, i.e., "Beckman Coulter Multisizer 3 Version 3.51" (Beckman Coulter, Inc.), for setting the measurement conditions and analyzing the measurement data, the weight-average particle diameter (D4) of the toner particle is determined by performing the measurement in 25,000 channels for the number of effective measurement channels and analyzing the measurement data.

The aqueous electrolyte solution used for the measurements is prepared by dissolving special-grade sodium chloride in deionized water to provide a concentration of approximately 1 mass % and, for example, "Isoton II" (Beckman Coulter, Inc.) can be used.

The dedicated software is configured as follows prior to measurement and analysis.

In the "modify the standard operating method (SOM)" screen in the dedicated software, the total count number in the control mode is set to 50,000 particles; the number of measurements is set to 1 time; and the Kd value is set to the value obtained using "standard particle 10.0 μm" (Beckman Coulter, Inc.). The threshold value and noise level are automatically set by pressing the threshold value/noise level measurement button. In addition, the current is set to 1,600 μA; the gain is set to 2; the electrolyte is set to Isoton II; and a check is entered for the post-measurement aperture tube flush.

In the "setting conversion from pulses to particle diameter" screen of the dedicated software, the bin interval is set to logarithmic particle diameter; the particle diameter bin is set to 256 particle diameter bins; and the particle diameter range is set to at least 2 μm and not more than 60 μm.

The specific measurement procedure is as follows.

(1) Approximately 200 mL of the above-described aqueous electrolyte solution is introduced into a 250-mL round-bottom glass beaker intended for use with the Multisizer 3 and this is placed in the sample stand and counterclockwise stirring with the stirrer rod is carried out at 24 rotations per second. Contamination and air bubbles within the aperture tube are preliminarily removed by the "aperture flush" function of the dedicated software.

(2) Approximately 30 mL of the above-described aqueous electrolyte solution is introduced into a 100-mL flatbottom glass beaker. To this is added as dispersing agent approximately 0.3 mL of a dilution prepared by the three-fold (mass) dilution with deionized water of "Contaminon N" (a 10 mass % aqueous solution of a neutral pH 7 detergent for cleaning precision measurement instrumentation, comprising a nonionic surfactant, anionic surfactant, and organic builder, Wako Pure Chemical Industries, Ltd.).

(3) A prescribed amount of deionized water is introduced into the water tank of an "Ultrasonic Dispersion System Tetora 150" (Nikkaki Bios Co., Ltd.), which is an ultrasound disperser with an electrical output of 120 W and equipped with two oscillators (oscillation frequency=50 kHz) disposed such that the phases are displaced by 180°, and approximately 2 mL of Contaminon N is added to this water tank.

(4) The beaker described in (2) is set into the beaker holder opening on the ultrasound disperser and the ultrasound disperser is started. The vertical position of the beaker is adjusted in such a manner that the resonance condition of the surface of the aqueous electrolyte solution within the beaker is at a maximum.

(5) While the aqueous electrolyte solution within the beaker set up according to (4) is being irradiated with ultrasound, approximately 10 mg of the toner is added to the aqueous electrolyte solution in small aliquots and dispersion is carried out. The ultrasound dispersion treatment is continued for an additional 60 seconds. The water temperature in the water tank is controlled as appropriate during ultrasound dispersion to be at least 10° C. and not more than 40° C.

(6) Using a pipette, the dispersed toner-containing aqueous electrolyte solution prepared in (5) is dripped into the roundbottom beaker set in the sample stand as described in (1) with adjustment to provide a measurement concentration of approximately 5%. Measurement is then performed until the number of measured particles reaches 50,000.

(7) The measurement data is analyzed by the previously cited dedicated software provided with the instrument and the weight-average particle diameter (D4) is calculated. When set to graph/volume % with the dedicated software, the "average diameter" on the analysis/volumetric statistical value (arithmetic average) screen is the weight-average particle diameter (D4).

EXAMPLES

The present invention is more specifically described by the production examples and examples that follow, but these in no way limit the present invention. Unless specifically indicated otherwise, parts and % in the following blends are on a mass basis in all instances.

Amorphous Polyester Production Example (1)

polyoxypropylene(2.2)-2,2-bis(4-hydroxyphenyl)propane: 71.1 parts (0.20 mol, 100.0 mol % with reference to the total number of moles of the alcohol component)

terephthalic acid: 29.9 parts (0.18 mol, 100.0 mol % with reference to the total number of moles of the carboxylic acid component)

titanium dihydroxybis(triethanolaminate): 0.72 parts per 100 parts of the overall amount of the monomer component These materials were weighed into a reaction vessel equipped with a condenser, stirrer, nitrogen introduction line, and thermocouple. The interior of the flask was then substituted with nitrogen gas followed by a gradual increase in the temperature while stirring. A reaction was run for 5 hours while stirring at a temperature of 200° C. to obtain an amorphous polyester resin (1).

The obtained amorphous polyester resin (1) had a weight-average molecular weight by GPC of 5,700. It had a softening point of 105° C., a glass transition temperature of 56° C., and an acid value of 6 mg KOH/g.

Amorphous Polyester Production Examples (2) to (15) and (17) to (31)

Amorphous polyester resins (2) to (15) and (17) to (31) were obtained by carrying out the reaction the same as in the Amorphous Polyester Production Example (1), but changing the alcohol component or carboxylic acid component used, the molar ratio, and the catalyst as shown in Table 1 and controlling the reaction time and reaction temperature so as to obtain the properties, e.g., Mw, given in Table 1. The mass parts of the starting materials was adjusted here so as to provide the same total number of moles for the alcohol component and carboxylic acid component as in Production Example (1). The properties of the obtained amorphous polyesters are given in Table 1.

Amorphous Polyester Production Example (16)

300 parts of ethyl acetate was introduced into a 5-L separable flask and 100 parts of the amorphous polyester (1) was gradually introduced thereinto and dissolution was carried out while stirring with a Three-One motor (Shinto Scientific Co., Ltd.). This was followed by the introduction of 0.72 parts of tin di(2-ethylhexanoate) and stirring, and amorphous polyester (16) was subsequently obtained by removal of the solvent under reduced pressure. The properties of the obtained amorphous polyester (16) are given in Table 1.

Amorphous Polyester Production Example (32)

300 parts of ethyl acetate was introduced into a 5-L separable flask and 100 parts of the amorphous polyester (17) was gradually introduced thereinto and dissolution was carried out while stirring with a Three-One motor (Shinto Scientific Co., Ltd.). This was followed by the introduction of 1.00 part of titanium dihydroxybis(triethanolaminate) and stirring, and amorphous polyester (32) was subsequently obtained by removal of the solvent under reduced pressure. The properties of the obtained amorphous polyester (32) are given in Table 1.

TABLE 1

| amorphous polyester No. | alcohol | | acid | | tin compound or titanium compound (number of parts per 100 parts of the monomer component) | | |
|---|---|---|---|---|---|---|---|
| | BPA-PO (2.2) | PG | terephthalic acid | adipic acid | tin dioctanoate | tin di(2-ethylhexanoate) | dibutyltin oxide |
| (1) | 100 mol % | 0 mol % | 100 mol % | — | — | — | — |
| (2) | 100 mol % | 0 mol % | 100 mol % | — | — | — | — |
| (3) | 100 mol % | 0 mol % | 100 mol % | — | — | — | — |
| (4) | 100 mol % | 0 mol % | 100 mol % | — | — | — | — |

TABLE 1-continued

| | | | | | | | |
|---|---|---|---|---|---|---|---|
| (5) | 100 mol % | 0 mol % | 100 mol % | — | — | — | — |
| (6) | 100 mol % | 0 mol % | 100 mol % | — | — | — | — |
| (7) | 100 mol % | 0 mol % | 100 mol % | — | — | — | — |
| (8) | 100 mol % | 0 mol % | 100 mol % | — | — | — | — |
| (9) | 100 mol % | 0 mol % | 100 mol % | — | — | — | — |
| (10) | 95 mol % | 5 mol % | 100 mol % | — | — | — | — |
| (11) | 85 mol % | 15 mol % | 100 mol % | — | — | — | — |
| (12) | 50 mol % | 50 mol % | 100 mol % | — | — | — | — |
| (13) | 0 mol % | 100 mol % | 100 mol % | — | — | — | — |
| (14) | 100 mol % | 0 mol % | 100 mol % | — | — | — | — |
| (15) | 100 mol % | 0 mol % | 100 mol % | — | — | — | — |
| (16) | 100 mol % | 0 mol % | 100 mol % | — | — | 0.72 | — |
| (17) | 100 mol % | 0 mol % | 95 mol % | 5 mol % | — | 0.50 | — |
| (18) | 100 mol % | 0 mol % | 95 mol % | 5 mol % | — | — | 0.40 |
| (19) | 100 mol % | 0 mol % | 95 mol % | 5 mol % | 0.28 | — | — |
| (20) | 100 mol % | 0 mol % | 95 mol % | 5 mol % | 0.85 | — | — |
| (21) | 100 mol % | 0 mol % | 95 mol % | 5 mol % | — | 0.12 | — |
| (22) | 100 mol % | 0 mol % | 95 mol % | 5 mol % | — | 1.20 | — |
| (23) | 100 mol % | 0 mol % | 95 mol % | 5 mol % | — | 0.60 | — |
| (24) | 100 mol % | 0 mol % | 95 mol % | 5 mol % | — | 0.80 | — |
| (25) | 100 mol % | 0 mol % | 95 mol % | 5 mol % | — | 0.70 | — |
| (26) | 100 mol % | 0 mol % | 95 mol % | 5 mol % | 0.64 | — | — |
| (27) | 95 mol % | 5 mol % | 95 mol % | 5 mol % | 0.68 | — | — |
| (28) | 85 mol % | 15 mol % | 95 mol % | 5 mol % | 0.70 | — | — |
| (29) | 50 mol % | 50 mol % | 95 mol % | 5 mol % | 0.65 | — | — |
| (30) | 0 mol % | 100 mol % | 95 mol % | 5 mol % | 0.60 | — | — |
| (31) | 100 mol % | 0 mol % | 95 mol % | 5 mol % | — | 0.06 | — |
| (32) | 100 mol % | 0 mol % | 100 mol % | — | — | 0.50 | — |

| amorphous polyester No. | tin compound or titanium compound (number of parts per 100 parts of the monomer component) | | | Mw | softening point Tm (° C.) | Tg (° C.) | acid value mgKOH/g |
|---|---|---|---|---|---|---|---|
| | titanium tetrabutoxide | titanium terephthalate | titanium dihydroxybis (triethanolaminate) | | | | |
| (1) | — | — | 0.72 | 5700 | 105 | 56 | 7 |
| (2) | 1.20 | — | — | 6000 | 100 | 55 | 5 |
| (3) | — | 1.00 | — | 5200 | 102 | 55 | 5 |
| (4) | — | — | 1.60 | 5500 | 100 | 56 | 7 |
| (5) | — | — | 0.50 | 6000 | 98 | 56 | 7 |
| (6) | — | — | 0.16 | 5200 | 104 | 56 | 6 |
| (7) | — | — | 1.80 | 4600 | 99 | 56 | 9 |
| (8) | — | — | 1.00 | 4000 | 100 | 56 | 10 |
| (9) | — | — | 1.40 | 6700 | 108 | 56 | 6 |
| (10) | — | — | 0.72 | 5600 | 105 | 56 | 7 |
| (11) | — | — | 0.68 | 5400 | 105 | 56 | 10 |
| (12) | — | — | 0.64 | 5200 | 104 | 54 | 16 |
| (13) | — | — | 0.60 | 5000 | 102 | 53 | 24 |
| (14) | — | — | 0.16 | 6000 | 106 | 56 | 7 |
| (15) | — | — | 1.40 | 8000 | 110 | 58 | 5 |
| (16) | — | — | 0.72 | 5700 | 105 | 54 | 6 |
| (17) | — | — | — | 5300 | 110 | 54 | 6 |
| (18) | — | — | — | 6200 | 107 | 55 | 8 |
| (19) | — | — | — | 6000 | 112 | 54 | 6 |
| (20) | — | — | — | 5209 | 109 | 54 | 6 |
| (21) | — | — | — | 5500 | 107 | 54 | 6 |
| (22) | — | — | — | 4700 | 112 | 54 | 9 |
| (23) | — | — | — | 4000 | 102 | 54 | 12 |
| (24) | — | — | — | 6900 | 112 | 57 | 5 |
| (25) | — | — | — | 8200 | 115 | 60 | 4 |
| (26) | — | — | — | 8200 | 115 | 60 | 4 |
| (27) | — | — | — | 8100 | 115 | 60 | 4 |
| (28) | — | — | — | 8300 | 115 | 59 | 4 |
| (29) | — | — | — | 8000 | 114 | 57 | 12 |
| (30) | — | — | — | 8500 | 116 | 57 | 15 |
| (31) | — | — | — | 4800 | 108 | 55 | 7 |
| (32) | — | — | 1.00 | 5300 | 110 | 54 | 6 |

The following abbreviations are used in the table.
BPA-PO(2.2): polyoxypropylene(2.2)-2,2-bis(4-hydroxyphenyl) propane
PG: propylene glycol Toner Production Example 1

| | |
|---|---|
| amorphous polyester resin (1) | 50 parts |
| amorphous polyester resin (17) | 50 parts |
| Fischer-Tropsch wax (peak temperature of maximum endothermic peak = 89° C.) | 5 parts |
| C.I. Pigment Blue 15:3 | 5 parts |
| aluminum 3,5-di-t-butylsalicylate compound | 0.5 parts |

Using a Henschel mixer (Model FM-75, Nippon Coke & Engineering Co., Ltd.), these materials were mixed at a rotation rate of 20 s$^{-1}$ for a rotation time of 5 minutes; this was followed by kneading at an output temperature of 130° C. using a twin-screw kneader (Model PCM-30, Ikegai Corp) set to a temperature of 120° C. The obtained kneaded material was cooled and coarsely pulverized to 1 mm and below using a hammer mill to obtain a coarsely pulverized material. The obtained coarsely pulverized material was finely pulverized using a mechanical pulverizer (T-250, Freund-Turbo Corporation). In addition, classification was carried out using a Faculty F-300 (Hosokawa Micron Corporation) to obtain a toner particle 1. The operating conditions were a classification rotor rotation rate of 130 s$^{-1}$ and a dispersing rotor rotation rate of 120 s$^{-1}$.

A toner 1 was obtained by adding, to 100 parts of the obtained toner particle 1, 1.0 part of hydrophobic silica fine particles that had a BET specific surface area of 25 m$^2$/g and that had undergone surface treatment with 4 mass % hexamethyldisilazane and 0.8 parts of hydrophobic silica fine particles that had a BET specific surface area of 100 m$^2$/g and that had undergone surface treatment with 10 mass % polydimethylsiloxane, and mixing with a Henschel mixer (Model FM-75, Nippon Coke & Engineering Co., Ltd.) at a rotation rate of 30 s$^{-1}$ for a rotation time of 10 minutes. Toner 1 had a weight-average particle diameter (D4) of 6.2 μm.

The Sn/Ti abundance ratio provided by x-ray fluorescence analysis for the Sn and Ti present in the amorphous polyester used in the Toner Production Example 1 was 61/39, and the total content of Sn and Ti was 1,100 ppm with reference to the mass of the amorphous polyester.

Toners 2 to 23 and 27 to 33 Production Example

Toners 2 to 23 and 27 to 33 were obtained proceeding as in the production example for toner 1, but changing the amorphous polyester used as a starting material and its number of parts as indicated in Table 2. Table 2 gives the Sn/Ti abundance ratio and content provided by x-ray fluorescence analysis for the Sn and Ti present in the amorphous polyesters used in the Toners 2 to 23 and 27 to 33 Production Example.

(Preparation of a Dispersion of Amorphous Polyester (1) Particles)

A mixed solvent of 250 parts of ethyl acetate and 50 parts of isopropyl alcohol was introduced into a 5-L separable flask; 200 parts of amorphous polyester (1) was gradually introduced thereinto; and an oil phase was obtained by dissolution with stirring with a Three-One motor (Shinto Scientific Co., Ltd.). Phase inversion emulsification was carried out by the dropwise addition of a suitable amount of a dilute aqueous ammonia solution to this stirred oil phase and the additional dropwise addition of 1,000 parts of deionized water. Solvent removal was carried out under reduced pressure using an evaporator to obtain a dispersion of amorphous polyester (1) particles.

(Preparation of a Dispersion of Amorphous Polyester (13) Particles, a Dispersion of Amorphous Polyester (17) Particles, and a Dispersion of Amorphous Polyester (30) Particles)

A dispersion of amorphous polyester (13) particles, a dispersion of amorphous polyester (17) particles, and a dispersion of amorphous polyester (30) particles were obtained proceeding as in the aforementioned Preparation of a Dispersion of Amorphous Polyester (1) Particles, but changing the amorphous polyester (1) used there to, respectively, amorphous polyester (13), amorphous polyester (17), and amorphous polyester (30).

(Preparation of a Wax Dispersion)

| | |
|---|---|
| deionized water | 800 parts |
| Fischer-Tropsch wax (maximum endothermic peak temperature = 89° C.) | 200 parts |
| anionic surfactant (Neogen RK, DKS Co., Ltd.) | 10 parts |

The preceding were heated to 95° C. and thoroughly dispersed using an Ultra-Turrax T50 from IKA, followed by dispersion processing with a pressure-ejection homogenizer to obtain a wax dispersion having a solids fraction of 20 mass %.

(Preparation of a Colorant Particle Dispersion)

| | |
|---|---|
| C.I. Pigment Blue 15:3 | (100 parts) |
| sodium dodecylbenzenesulfonate | (5 parts) |
| deionized water | (400 parts) |

These were mixed and were dispersed using a sand grinder mill to obtain a colorant particle dispersion.

Toner Production Example 24

| | |
|---|---|
| dispersion of amorphous polyester (13) particles | 700 parts |
| dispersion of amorphous polyester (30) particles | 300 parts |
| colorant particle dispersion | 40 parts |
| wax dispersion | 50 parts |
| sodium dodecylbenzenesulfonate | 5 parts |

The dispersion of amorphous polyester (13) particles, the dispersion of amorphous polyester (30) particles, the wax dispersion, and the sodium dodecylbenzenesulfonate were introduced into a reactor (flask with a 1 liter volume, baffled, anchor impeller) and were mixed to uniformity. Otherwise, the colorant particle dispersion was mixed to uniformity in a 500-mL beaker, and this was gradually added to the reactor while stirring to obtain a mixed dispersion. While the obtained mixed dispersion was being stirred, 0.5 parts as solids of an aqueous aluminum sulfate solution was added dropwise to induce the formation of aggregate particles.

After the completion of the dropwise addition, the interior of the system was substituted using nitrogen and holding was carried out for 1 hour at 50° C. and for 1 hour at 55° C. The temperature was then raised and holding was carried out for 30 minutes at 90° C. The temperature was subsequently reduced to 63° C. followed by holding for 3 hours to induce the formation of fused particles. The reaction here was carried out under a nitrogen atmosphere. After the prescribed period of time was finished, cooling to room temperature was carried out at a cooling rate of 0.5° C. per minute.

After cooling, the reaction product was subjected to solid-liquid separation at a pressure of 0.4 MPa on a pressure filter having a volume of 10 L to obtain a toner cake. Deionized water was then added to the pressure filter to the full level and washing was performed at a pressure of 0.4 MPa. Washing in this manner was carried out a total of three times. This toner cake was dispersed in 1 L of a 50:50 mixed solvent of methanol/water in which 0.15 parts of a nonionic surfactant 1 was dissolved to obtain a dispersion of surface-treated toner particles.

This toner particle dispersion was poured into a pressure filter and 5 L of deionized water was added. Solid-liquid separation was then performed at a pressure of 0.4 MPa, after which fluidized bed drying was carried out at 45° C. to obtain a toner particle 24.

A toner 24 was obtained by adding, to 100 parts of the obtained toner particle 24, 1.0 part of hydrophobic silica fine particles that had a BET specific surface area of 25 m$^2$/g and that had undergone surface treatment with 4 mass % hexamethyldisilazane and 0.8 parts of hydrophobic silica fine particles that had a BET specific surface area of 100 m$^2$/g and that had undergone surface treatment with 10 mass % polydimethylsiloxane, and mixing with a Henschel mixer (Model FM-75, Nippon Coke & Engineering Co., Ltd.) at a rotation rate of 30 s$^{-1}$ for a rotation time of 10 minutes. Toner 24 had a weight-average particle diameter (D4) of 6.2 μm. The Sn/Ti abundance ratio provided by x-ray fluorescence analysis for the Sn and Ti present in the amorphous polyester used in Toner Production Example 24 was 51/49, and the total content of Sn and Ti was 1,000 ppm with reference to the mass of the amorphous polyester.

Toner Production Example 25

A toner 25 was obtained proceeding as in the Toner Production Example 24, but changing the amorphous polyester (13) particle dispersion to the amorphous polyester (1) particle dispersion and changing the amorphous polyester (30) particle dispersion to the amorphous polyester (26) particle dispersion. Toner 25 had a weight-average particle diameter (D4) of 6.2 μm. The Sn/Ti abundance ratio provided by x-ray fluorescence analysis for the Sn and Ti present in the amorphous polyester used in Toner Production Example 25 was 46/54, and the total content of Sn and Ti was 1,100 ppm with reference to the mass of the amorphous polyester.

Toner Production Example 26

A toner 26 was obtained proceeding as in the Toner Production Example 24, but changing the amorphous polyester (13) particle dispersion to 500 parts of the amorphous polyester (1) particle dispersion and changing the amorphous polyester (30) particle dispersion to 500 parts of the amorphous polyester (17) particle dispersion. Toner 26 had a weight-average particle diameter (D4) of 6.2 μm. The Sn/Ti abundance ratio provided by x-ray fluorescence analysis for the Sn and Ti present in the amorphous polyester used in Toner Production Example 26 was 61/39.

TABLE 2

| | amorphous polyester (per total of 100 parts) | | | | | | Sn/Ti in the amorphous polyester | total abundance of tin and titanium (ppm) | toner production method |
|---|---|---|---|---|---|---|---|---|---|
| toner No. | resin 1 used amorphous polyester No. | parts | resin 2 used amorphous polyester No. | parts | resin 3 used amorphous polyester No. | parts | | | |
| 1 | (1) | 50 | (17) | 50 | | | 61/39 | 1100 | pulverization |
| 2 | (32) | 50 | (17) | 50 | | | 70/30 | 2000 | pulverization |
| 3 | (1) | 50 | (16) | 50 | | | 54/46 | 1900 | pulverization |
| 4 | (1) | 20 | (17) | 40 | (26) | 40 | 38/62 | 1400 | pulverization |
| 5 | (2) | 50 | (17) | 50 | | | 47/53 | 1500 | pulverization |
| 6 | (3) | 50 | (17) | 50 | | | 39/61 | 1800 | pulverization |
| 7 | (1) | 40 | (18) | 60 | | | 68/32 | 1400 | pulverization |
| 8 | (1) | 28 | (17) | 72 | | | 74/26 | 1200 | pulverization |
| 9 | (1) | 83 | (17) | 17 | | | 28/72 | 1000 | pulverization |
| 10 | (4) | 52 | (19) | 48 | | | 25/75 | 1400 | pulverization |
| 11 | (5) | 52 | (20) | 48 | | | 77/23 | 1400 | pulverization |
| 12 | (6) | 50 | (21) | 50 | | | 60/40 | 200 | pulverization |
| 13 | (7) | 50 | (22) | 50 | | | 61/39 | 2800 | pulverization |
| 14 | (8) | 50 | (23) | 50 | | | 59/41 | 1400 | pulverization |
| 15 | (9) | 50 | (24) | 50 | | | 58/42 | 2000 | pulverization |
| 16 | (9) | 50 | (25) | 50 | | | 54/46 | 1800 | pulverization |
| 17 | (1) | 50 | (26) | 50 | | | 67/33 | 1300 | pulverization |
| 18 | (1) | 70 | (26) | 30 | | | 46/54 | 1100 | pulverization |
| 19 | (17) | 50 | (15) | 50 | | | 45/55 | 1500 | pulverization |
| 20 | (10) | 70 | (27) | 30 | | | 48/52 | 1200 | pulverization |
| 21 | (11) | 70 | (28) | 30 | | | 52/48 | 1100 | pulverization |
| 22 | (12) | 70 | (29) | 30 | | | 50/50 | 1100 | pulverization |
| 23 | (13) | 70 | (30) | 30 | | | 51/49 | 1000 | pulverization |
| 24 | (13) | 70 | (30) | 30 | | | 51/49 | 1000 | aggregation |
| 25 | (1) | 70 | (26) | 30 | | | 46/54 | 1100 | aggregation |
| 26 | (1) | 50 | (17) | 50 | | | 61/39 | 1100 | aggregation |
| 27 | (17) | 50 | (21) | 50 | | | 100/0 | 800 | pulverization |
| 28 | (1) | 50 | (4) | 50 | | | 0/100 | 1400 | pulverization |
| 29 | (1) | 20 | (17) | 80 | | | 86/14 | 1300 | pulverization |
| 30 | (1) | 88 | (17) | 12 | | | 15/85 | 900 | pulverization |
| 31 | (1) | 50 | (31) | 50 | | | 10/90 | 500 | pulverization |
| 32 | (14) | 50 | (17) | 50 | | | 88/12 | 800 | pulverization |
| 33 | (15) | 50 | (25) | 50 | | | 54/46 | 1800 | pulverization |

Magnetic Core Particle 1 Production Example

Step 1 (Weighing•Mixing Step):

| | |
|---|---|
| $Fe_2O_3$ | 62.7 parts |
| $MnCO_3$ | 29.5 parts |
| $Mg(OH)_2$ | 6.8 parts |
| $SrCO_3$ | 1.0 part |

The ferrite starting materials were weighed out so that these materials assumed the composition ratio given above. This was followed by pulverization and mixing for 5 hours using a dry vibrating mill using stainless steel beads having a diameter of ⅛-inch.

Step 2 (Pre-Firing Step):

The obtained pulverizate was converted into approximately 1 mm-square pellets using a roller compactor. After removal of the coarse powder using a vibrating screen having an aperture of 3 mm and subsequent removal of the fines using a vibrating screen having an aperture of 0.5 mm, the pellets were fired for 4 hours at a temperature of 1,000° C. in a burner-type firing furnace under a nitrogen atmosphere (oxygen concentration: 0.01 volume %) to produce a pre-fired ferrite. The composition of the resulting pre-fired ferrite was as follows.

$$(MnO)_a(MgO)_b(SrO)_c(Fe_2O_3)_d$$

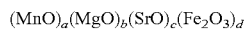

In this formula, a=0.257, b=0.117, c=0.007, d=0.393

Step 3 (Pulverization Step):

The resulting pre-fired ferrite was pulverized to approximately 0.3 mm with a crusher followed by pulverization for 1 hour with a wet ball mill using zirconia beads with a diameter of ⅛-inch and with the addition of 30 parts water per 100 parts of the pre-fired ferrite. The obtained slurry was milled for 4 hours using a wet ball mill using alumina beads with a diameter of 1/16-inch to obtain a ferrite slurry (finely pulverized pre-fired ferrite).

Step 4 (Granulation Step):

1.0 part of an ammonium polycarboxylate as a dispersing agent and 2.0 parts of polyvinyl alcohol as a binder per 100 parts of the pre-fired ferrite were added to the ferrite slurry, followed by granulation with a spray dryer (manufacturer: Ohkawara Kakohki Co., Ltd.) into spherical particles. Particle size adjustment was carried out on the obtained particles, which were subsequently heated for 2 hours at 650° C. using a rotary kiln to remove the dispersing agent and binder organic components.

Step 5 (Firing Step):

In order to control the firing atmosphere, the temperature was raised over 2 hours from room temperature to a temperature of 1,300° C. in an electric furnace under a nitrogen atmosphere (oxygen concentration: 1.00 volume %); firing was then carried out for 4 hours at a temperature of 1,150° C. This was followed by cooling to a temperature of 60° C. over 4 hours; returning to the atmosphere from the nitrogen atmosphere; and removal at a temperature at or below 40° C.

Step 6 (Classification Step):

After the aggregated particles had been crushed, the weakly magnetic fraction was cut out by magnetic separation and the coarse particles were removed by sieving on a sieve with an aperture of 250 μm to obtain a magnetic core particle 1 having a 50% particle diameter on a volume basis (D50) of 37.0 μm.

Preparation of Coating Resin 1

| | |
|---|---|
| cyclohexyl methacrylate monomer | 26.8 mass % |
| methyl methacrylate monomer | 0.2 mass % |
| methyl methacrylate macromonomer (macromonomer having a weight-average molecular weight of 5,000 and having the methacryloyl group at one terminal) | 8.4 mass % |
| toluene | 31.3 mass % |
| methyl ethyl ketone | 31.3 mass % |
| azobisisobutyronitrile | 2.0 mass % |

Of these materials, the cyclohexyl methacrylate, methyl methacrylate, methyl methacrylate macromonomer, toluene, and methyl ethyl ketone were introduced into a four-neck separable flask fitted with a reflux condenser, thermometer, nitrogen introduction line, and stirring apparatus; nitrogen gas was introduced to thoroughly convert into a nitrogen atmosphere; heating to 80° C. was carried out; and the azobisisobutyronitrile was added and polymerization was performed for 5 hours under reflux. The copolymer was precipitated by pouring hexane into the obtained reaction product and the precipitate was separated by filtration and then vacuum dried to obtain a coating resin 1. 30 parts of the coating resin 1 was subsequently dissolved in 40 parts of toluene and 30 parts of methyl ethyl ketone to obtain a polymer solution 1 (30 mass % solids fraction).

Preparation of Coating Resin Solution 1

| | |
|---|---|
| polymer solution 1 (30% resin solids concentration) | 33.3 mass % |
| toluene | 66.4 mass % |
| carbon black (Regal 330, Cabot Corporation) (primary particle diameter = 25 nm, specific surface area by nitrogen adsorption = 94 m²/g, DBF absorption = 75 mL/100 g) | 0.3 mass % | were dispersed for 1 hour using a paint shaker and zirconia beads having a diameter of 0.5 mm. The obtained dispersion was filtered on a 5.0-μm membrane filter to obtain a coating resin solution 1.

Magnetic Carrier 1 Production Example (Resin Coating Step):

The coating resin solution 1 was introduced into a vacuum-degassed kneader being maintained at normal temperature so as to provide 2.5 parts as the resin component with reference to the magnetic core particle 1 (100 mass parts). After introduction, stirring was performed for 15 minutes at a rotation rate of 30 rpm and, after at least a certain amount (80 mass %) of the solvent had been evaporated, the temperature was raised to 80° C. while mixing under reduced pressure and the toluene was distilled off over 2 hours followed by cooling. The obtained magnetic carrier, after fractionation and separation of the weakly magnetic product by magnetic selection and passage through a screen with an aperture of 70 μm, was classified using an air classifier to obtain a magnetic carrier 1 having a 50% particle diameter on a volume basis (D50) of 38.2 μm.

Two-Component Developer Production Example 1

Toner 1 (8.0 parts) was added to magnetic carrier 1 (92.0 parts) and mixing was performed using a V-mixer (V-20, Seishin Enterprise Co., Ltd.) to obtain a two-component developer 1.

Two-Component Developer Production Examples 2 to 33

Two-component developers 2 to 33 were obtained by carrying out production as in the Two-Component Developer Production Example 1, but changing the toner as shown in Table 3.

TABLE 3

| two-component developer | toner | carrier |
|---|---|---|
| two-component developer 1 | toner 1 | magnetic carrier 1 |
| two-component developer 2 | toner 2 | magnetic carrier 1 |
| two-component developer 3 | toner 3 | magnetic carrier 1 |
| two-component developer 4 | toner 4 | magnetic carrier 1 |
| two-component developer 5 | toner 5 | magnetic carrier 1 |
| two-component developer 6 | toner 6 | magnetic carrier 1 |
| two-component developer 7 | toner 7 | magnetic carrier 1 |
| two-component developer 8 | toner 8 | magnetic carrier 1 |
| two-component developer 9 | toner 9 | magnetic carrier 1 |
| two-component developer 10 | toner 10 | magnetic carrier 1 |
| two-component developer 11 | toner 11 | magnetic carrier 1 |
| two-component developer 12 | toner 12 | magnetic carrier 1 |
| two-component developer 13 | toner 13 | magnetic carrier 1 |
| two-component developer 14 | toner 14 | magnetic carrier 1 |
| two-component developer 15 | toner 15 | magnetic carrier 1 |
| two-component developer 16 | toner 16 | magnetic carrier 1 |
| two-component developer 17 | toner 17 | magnetic carrier 1 |
| two-component developer 18 | toner 18 | magnetic carrier 1 |
| two-component developer 19 | toner 19 | magnetic carrier 1 |
| two-component developer 20 | toner 20 | magnetic carrier 1 |
| two-component developer 21 | toner 21 | magnetic carrier 1 |
| two-component developer 22 | toner 22 | magnetic carrier 1 |
| two-component developer 23 | toner 23 | magnetic carrier 1 |
| two-component developer 24 | toner 24 | magnetic carrier 1 |
| two-component developer 25 | toner 25 | magnetic carrier 1 |
| two-component developer 26 | toner 26 | magnetic carrier 1 |
| two-component developer 27 | toner 27 | magnetic carrier 1 |
| two-component developer 28 | toner 28 | magnetic carrier 1 |
| two-component developer 29 | toner 29 | magnetic carrier 1 |
| two-component developer 30 | toner 30 | magnetic carrier 1 |
| two-component developer 31 | toner 31 | magnetic carrier 1 |
| two-component developer 32 | toner 32 | magnetic carrier 1 |
| two-component developer 33 | toner 33 | magnetic carrier 1 |

[1. Evaluation of the Hot Offset Resistance]

An imageRUNNER ADVANCE C9075PRO full-color copier from Canon Inc. was modified to enable the fixation temperature and process speed to be freely set, and a test of the fixation temperature range was carried out using the two-component developer 1. With regard to the image, unfixed images were produced in single-color mode in a normal-temperature, normal-humidity environment (temperature=23° C., relative humidity=50% to 60%) with the toner laid-on level on the paper adjusted to 1.2 mg/cm$^2$. GF-C081 copy paper (A4, areal weight=81.4 g/m$^2$, marketed by Canon Marketing Japan Inc.) was used as the evaluation paper, and an image was formed that had an image print percentage of 25%.

The formed images were then fixed in a normal-temperature, low-humidity environment (temperature=23° C., relative humidity not more than 5%) with the process speed set to 450 mm/second and raising the fixation temperature in 5° C. steps in sequence from 120° C. The upper limit temperature at which offset was not produced was taken to be the hot offset resistance temperature.

The hot offset resistance temperature was ranked using the following criteria. The results of the evaluation are given in Table 4.

(Evaluation Criteria for the Hot Offset Resistance Temperature)
A: at least 210° C. (extremely good)
B: at least 200° C. and less than 210° C. (good)
C: at least 190° C. and less than 200° C. (the effects of the present invention are being obtained)
D: less than 190° C.

[2. Evaluation of the Fixing Wraparound Resistance]

Using the evaluation machine used in the aforementioned evaluation of the hot offset resistance, an unfixed image (toner laid-on level=1.2 mg/cm$^2$) having a length of 60 mm in the direction of paper transit was formed starting at a location 1 mm from the leading edge of the evaluation paper. Using the same adjustments, 10 sheets of the evaluation sample carrying the unfixed image were produced. CS-680 (A4, areal weight=68.0 g/m$^2$, marketed by Canon Marketing Japan Inc.) was used as the evaluation paper.

Then, operating in a high-temperature, high-humidity environment (temperature=30° C., relative humidity=80%), the 10 sheets were continuously fed through at a paper transport speed of 450 mm/second with the fixation temperature being raised in 5° C. steps in sequence from 150° C. The upper limit temperature at which wraparound during fixing was not produced was taken to be the fixing wraparound resistance temperature. The results of the evaluation were ranked according to the following criteria. The results of the evaluation are given in Table 4.

A: at least 200° C. (very good)
B: at least 185° C. and less than 200° C. (good)
C: at least 170° C. and less than 185° C. (the effects of the present invention are being obtained)
D: less than 170° C.

[3. Evaluation of the Low-Temperature Fixability]

A test of the low-temperature fixability was performed using the two-component developer 1 and the evaluation machine used in the aforementioned evaluation of the hot offset resistance. With regard to the image, unfixed images were produced in single-color mode in a normal-temperature, normal-humidity environment (temperature=23° C., relative humidity of at least 50% and not more than 60%) with the toner laid-on level on the paper adjusted to 1.2 mg/cm$^2$. GF-C081 copy paper (A4, areal weight=81.4 g/m$^2$, marketed by Canon Marketing Japan Inc.) was used as the evaluation paper, and an image was formed that had an image print percentage of 25%.

Then, operating in a low-temperature, low-humidity environment (temperature=15° C., relative humidity not more than 10%) with the process speed set to 450 mm/second and raising the fixation temperature in 5° C. steps in sequence from 120° C., the low-temperature fixation temperature was taken to be the lower limit temperature at which offset was not produced.

(Criteria for Evaluating the Low-Temperature Fixation Temperature)
A: less than 150° C. (very good)
B: at least 150° C. and less than 160° C. (good)
C: at least 160° C. and less than 170° C. (the effects of the present invention are being obtained)
D: at least 170° C.

[4. Evaluation of the Charge Stability]

The evaluation described below was carried out using an ImagePress C800 full-color copier from Canon Inc. as the image-forming apparatus, with the aforementioned two-component developer charged to the cyan developing device of the image-forming apparatus. A modification was made by removing the mechanism that discharged, from the developing device, the excess magnetic carrier within the developing device.

Adjustments were made so the toner laid-on level on the paper for the FFh image (solid image) was 0.45 mg/cm$^2$. FFh refers to values that express 256 gradations in hexadecimal format, wherein 00h is the first gradation (white background) of the 256 gradations and FF is the 256th gradation (solid region) of the 256 gradations.

A 10,000-print image output durability test was carried out at an image ratio of 25% in a normal-temperature, normal-humidity (NN) environment (temperature=23° C., relative humidity of at least 50% and not more than 60%) as an image output durability test. During the 10,000-sheet continuous paper feed, the paper was fed using the same developing conditions as for the 1st sheet (no calibration). GF-C081 plain copy paper (A4, areal weight=81.4 g/m$^2$, marketed by Canon Marketing Japan Inc.) was used for the evaluation paper in the 10,000-print image output durability test.

The evaluation criteria and the item evaluated on the output image, both initially (1st print) and after a 10,000-sheet continuous paper feed, are given below. The results of the evaluation are given in Table 4.

(Measurement of the Image Density)

Using an X-Rite color reflection densitometer (500 Series, X-Rite, Inc.), the image density of the FFh image area: solid area was measured both initially (1st print) and on the 10,000th print, and the ranking was scored using the following criteria based on the difference Δ between the two image densities. The results of the evaluations are given in Table 4.

A: less than 0.05 (very good)

B: at least 0.05 and less than 0.10 (good)

C: at least 0.10 and less than 0.15 (the effects of the present invention are being obtained)

D: at least 0.15

Examples 2 to 26 and Comparative Examples 1 to 7

Evaluations were carried out proceeding as in Example 1, but changing the two-component developer used in the evaluations to the two-component developers indicated in Table 3. The results of the evaluations are given in Table 4.

TABLE 4

| Example No. | two-component developer No. | hot offset resistance | rank | fixing wraparound resistance | rank | low-temperature fixability | rank | density difference after NN durability test (%) | rank |
|---|---|---|---|---|---|---|---|---|---|
| 1 | 1 | 225 | A | 210 | A | 150 | B | 0.03 | A |
| 2 | 2 | 210 | A | 195 | B | 150 | B | 0.03 | A |
| 3 | 3 | 210 | A | 195 | B | 150 | B | 0.04 | A |
| 4 | 4 | 215 | A | 205 | A | 150 | B | 0.04 | A |
| 5 | 5 | 220 | A | 205 | A | 150 | B | 0.04 | A |
| 6 | 6 | 220 | A | 205 | A | 150 | B | 0.04 | A |
| 7 | 7 | 200 | B | 185 | B | 150 | B | 0.04 | A |
| 8 | 8 | 195 | C | 175 | C | 150 | B | 0.07 | B |
| 9 | 9 | 195 | C | 175 | C | 150 | B | 0.06 | B |
| 10 | 10 | 195 | C | 175 | C | 150 | B | 0.07 | B |
| 11 | 11 | 195 | C | 175 | C | 150 | B | 0.07 | B |
| 12 | 12 | 200 | B | 185 | B | 150 | B | 0.06 | B |
| 13 | 13 | 225 | A | 205 | A | 145 | A | 0.09 | B |
| 14 | 14 | 220 | A | 205 | A | 145 | A | 0.07 | B |
| 15 | 15 | 205 | B | 185 | B | 155 | B | 0.04 | A |
| 16 | 16 | 195 | C | 170 | C | 160 | C | 0.03 | A |
| 17 | 17 | 200 | B | 200 | A | 155 | B | 0.03 | A |
| 18 | 18 | 205 | B | 205 | A | 155 | B | 0.03 | A |
| 19 | 19 | 200 | B | 200 | A | 155 | B | 0.03 | A |
| 20 | 20 | 205 | B | 200 | A | 155 | B | 0.04 | A |
| 21 | 21 | 205 | B | 190 | B | 155 | B | 0.04 | A |
| 22 | 22 | 200 | B | 185 | B | 155 | B | 0.07 | B |
| 23 | 23 | 200 | B | 185 | B | 155 | B | 0.09 | B |
| 24 | 24 | 195 | C | 175 | C | 155 | B | 0.12 | C |
| 25 | 25 | 205 | B | 180 | C | 155 | B | 0.10 | C |
| 26 | 26 | 210 | A | 195 | B | 150 | B | 0.09 | B |
| Comparative 1 | 27 | 180 | D | 165 | D | 155 | B | 0.12 | C |
| Comparative 2 | 28 | 180 | D | 165 | D | 155 | B | 0.13 | C |
| Comparative 3 | 29 | 180 | D | 165 | D | 155 | B | 0.12 | C |
| Comparative 4 | 30 | 180 | D | 165 | D | 155 | B | 0.12 | C |
| Comparative 5 | 31 | 180 | D | 165 | D | 155 | B | 0.10 | C |
| Comparative 6 | 32 | 180 | D | 165 | D | 155 | B | 0.10 | C |
| Comparative 7 | 33 | 185 | D | 165 | D | 170 | D | 0.06 | B |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-105086, filed May 26, 2016, which is hereby incorporated by reference herein in its entirety.

What is claimed is:

1. A method of producing a toner comprising a toner particle containing an amorphous polyester, the toner production method comprising:
   a step of melt-kneading the amorphous polyester; and
   a step of pulverizing the obtained kneaded material, wherein
   the amorphous polyester contains an amorphous polyester 1, the amorphous polyester further contains an amorphous polyester 2, the amorphous polyester 1 contains either one of a tin compound and a titanium compound, the amorphous polyester 2 contains the other of the tin compound and the titanium compound, in the step of melt-kneading the amorphous polyester, both the amorphous polyester 1 and the amorphous polyester 2 are melt-kneaded, a Sn/Ti abundance ratio between Sn and Ti in the amorphous polyester according to x-ray fluorescence analysis is 20/80 to 80/20, a weight-average molecular weight $Mw1$ of the amorphous polyester 1 according to measurement by gel permeation chromatography (GPC) is $Mw1<7,000$, the tin compound does not contain a Sn—C bond, and the titanium compound has an alkanolamine-derived residue.

2. The method according to claim 1, wherein the titanium compound is titanium dihydroxybis(triethanolaminate).

3. The method according to claim 1, wherein the tin compound is tin alkylcarboxylate.

4. The method according to claim 1, wherein the titanium compound is titanium dihydroxybis(triethanolaminate), and the tin compound is tin alkylcarboxylate.

* * * * *